(12) United States Patent
Wang

(10) Patent No.: US 10,899,842 B2
(45) Date of Patent: Jan. 26, 2021

(54) 4-1BB BINDING PROTEINS AND USES THEREOF

(71) Applicant: IMMUNOAH THERAPEUTICS, INC., Aurora, CO (US)

(72) Inventor: Min Wang, Cherry Hills Village, CO (US)

(73) Assignee: IMMUNOAH THERAPEUTICS, INC., Aurora, CO (US)

( * ) Notice: Subject to any disclaimer, the term of this patent is extended or adjusted under 35 U.S.C. 154(b) by 0 days.

(21) Appl. No.: 16/463,580

(22) PCT Filed: Nov. 22, 2017

(86) PCT No.: PCT/US2017/063142
§ 371 (c)(1),
(2) Date: May 23, 2019

(87) PCT Pub. No.: WO2018/098370
PCT Pub. Date: May 31, 2018

(65) Prior Publication Data
US 2019/0284292 A1 Sep. 19, 2019

Related U.S. Application Data

(60) Provisional application No. 62/426,074, filed on Nov. 23, 2016.

(51) Int. Cl.
*C07K 16/28* (2006.01)
*A61P 35/00* (2006.01)
*A61K 39/00* (2006.01)

(52) U.S. Cl.
CPC .......... *C07K 16/2878* (2013.01); *A61P 35/00* (2018.01); *A61K 2039/505* (2013.01); *A61K 2039/545* (2013.01); *C07K 2317/21* (2013.01); *C07K 2317/33* (2013.01); *C07K 2317/34* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,816,397 A | 3/1989 | Boss et al. |
| 4,816,567 A | 3/1989 | Cabilly et al. |
| 4,880,078 A | 11/1989 | Inoue et al. |
| 4,980,286 A | 12/1990 | Morgan et al. |
| 5,128,326 A | 7/1992 | Balazs et al. |
| 5,225,539 A | 7/1993 | Winter |
| 5,290,540 A | 3/1994 | Prince et al. |
| 5,530,101 A | 6/1996 | Queen et al. |
| 5,565,332 A | 10/1996 | Hoogenboom et al. |
| 5,585,089 A | 12/1996 | Queen et al. |
| 5,624,821 A | 4/1997 | Winter et al. |
| 5,648,260 A | 7/1997 | Winter et al. |
| 5,679,377 A | 10/1997 | Bernstein et al. |
| 5,693,762 A | 12/1997 | Queen et al. |
| 5,714,350 A | 2/1998 | Co et al. |
| 5,714,352 A | 2/1998 | Jakobovits |
| 5,723,323 A | 3/1998 | Kauffman et al. |
| 5,763,192 A | 6/1998 | Kauffman et al. |
| 5,766,886 A | 6/1998 | Studnicka et al. |
| 5,807,715 A | 9/1998 | Morrison et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,855,913 A | 1/1999 | Hanes et al. |
| 5,874,064 A | 2/1999 | Edwards et al. |
| 5,912,015 A | 6/1999 | Bernstein et al. |
| 5,916,597 A | 6/1999 | Lee et al. |
| 5,934,272 A | 8/1999 | Lloyd et al. |
| 5,976,862 A | 11/1999 | Kauffman et al. |
| 5,985,309 A | 11/1999 | Edwards et al. |
| 5,985,320 A | 11/1999 | Edwards |
| 5,989,463 A | 11/1999 | Tracy et al. |
| 6,019,968 A | 2/2000 | Platz et al. |
| 6,180,370 B1 | 1/2001 | Queen et al. |
| 6,204,023 B1 | 3/2001 | Robinson et al. |
| 6,350,861 B1 | 2/2002 | Co et al. |
| 6,660,843 B1 | 12/2003 | Feige et al. |
| 8,337,850 B2 | 12/2012 | Ahrens et al. |
| 2002/0137134 A1 | 9/2002 | Gerngross |
| 2004/0018590 A1 | 1/2004 | Gerngross et al. |
| 2005/0042664 A1 | 2/2005 | Wu et al. |
| 2006/0104968 A1 | 5/2006 | Bookbinder et al. |

(Continued)

FOREIGN PATENT DOCUMENTS

| | | |
|---|---|---|
| EP | 0239400 A2 | 9/1987 |
| EP | 0592106 A1 | 4/1994 |

(Continued)

OTHER PUBLICATIONS

Azzazy et al. (2002) "Phage display technology: clinical applications and recent innovations," Clin. Biochem, 35, pp. 425-445.
Bird et al. (1988) "Single-Chain Antigen-Binding Proteins," Science, 242, pp. 423-426.
Buchwald et al., 1980, "Long-term, continuous intravenous heparin administration by an implantable infusion pump in ambulatory patients with recurrent venous thrombosis," Surgery, 88, pp. 507. (Abstract Only).
Carter et al. (1992) "Humanization of an anti-p185HER2 antibody for human cancer therapy," Proc. Natl. Acad. Sci. U.S.A., 89, 5 pp.
Chothia et al. (1987) "Canonical Structures for the Hypervariable Regions of Immunoglobulins," J. Mol. Biol., 196, 17 pp.

(Continued)

*Primary Examiner* — Padmavathi Baskar
(74) *Attorney, Agent, or Firm* — Lathrop GPM LLP

(57) ABSTRACT

Binding proteins that specifically bind to 4-1BB (CD137) are disclosed. More specifically, antibodies that specifically bind to human 4-1BB are disclosed. These binding proteins may be used to treat or to prevent diseases such as cancers by altering the levels or activities of 4-1BB.

19 Claims, 10 Drawing Sheets

Specification includes a Sequence Listing.

(56) References Cited

U.S. PATENT DOCUMENTS

| | | |
|---|---|---|
| 2009/0092612 A1 | 4/2009 | Takayama et al. |
| 2012/0177664 A1 | 7/2012 | Yokoseki et al. |
| 2012/0237498 A1 | 9/2012 | Ahrens et al. |

FOREIGN PATENT DOCUMENTS

| | | | |
|---|---|---|---|
| EP | 1176195 A1 | 1/2002 | |
| WO | WO 1990/005144 A1 | 5/1990 | |
| WO | WO 1990/014424 A1 | 11/1990 | |
| WO | WO 1990/014430 A1 | 11/1990 | |
| WO | WO 1990/014443 A1 | 11/1990 | |
| WO | WO 1991/005548 A1 | 5/1991 | |
| WO | WO 1991/009967 A1 | 7/1991 | |
| WO | WO 1992/001047 A1 | 1/1992 | |
| WO | WO 1992/003461 A1 | 3/1992 | |
| WO | WO 1992/011272 A1 | 7/1992 | |
| WO | WO 1992/019244 A2 | 11/1992 | |
| WO | WO 1993/006213 A1 | 4/1993 | |
| WO | WO 1994/018219 A1 | 8/1994 | |
| WO | WO 1996/020698 A2 | 7/1996 | |
| WO | WO 1997/020032 A1 | 6/1997 | |
| WO | WO 1997/032572 A2 | 9/1997 | |
| WO | WO 1997/044013 A1 | 11/1997 | |
| WO | WO 1998/031346 A1 | 7/1998 | |
| WO | WO 1999/006834 A2 | 2/1999 | |
| WO | WO 1999/015154 A1 | 4/1999 | |
| WO | WO 1999/020253 A1 | 4/1999 | |
| WO | WO 1999/025044 A1 | 5/1999 | |
| WO | WO 1999/066903 A2 | 12/1999 | |
| WO | WO 2001/083525 A2 | 11/2001 | |
| WO | WO 2002/072636 A2 | 9/2002 | |
| WO | WO 2003/016466 A2 | 2/2003 | |
| WO | WO 2003/035835 A2 | 5/2003 | |
| WO | WO 2004/078140 A2 | 9/2004 | |
| WO | WO 2005/007699 A2 | 1/2005 | |
| WO | WO 2005/100584 A2 | 10/2005 | |
| WO | WO 2005/123126 A2 | 12/2005 | |
| WO | WO 2007/014162 A2 | 2/2007 | |
| WO | WO 2012032433 A1 | 3/2012 | |
| WO | WO 2016/134358 A1 | 8/2016 | |

OTHER PUBLICATIONS

Chothia et al. (1989) "Conformations of immunoglobulin hypervariable regions," Nature, 342, 7 pp.
Co et al. (1993) "Genetically engineered deglycosylation of the variable domain increases the affinity of an anti-cd33 monoclonal antibody," Mol. Immunol., 30, pp. 1361-1367.
During et al. (1989) "Controlled Release of Dopamine from a Polymeric Brain Implant: In Vivo Characterization" Ann. Neurol., 25, 6 pp.
Durocher et al. (2002) "High-level and high-throughput recombinant protein production by transient transfection of suspension-growing human 293-EBNA1 cells" Nucleic Acids Research, vol. 30, No. 2., 9 pp.
Foote et al. (1992) "Antibody Framework Residues Affecting the Conformation of the Hypervariable Loops," J. Mol. Biol., 224, pp. 487-499.
Gavilondo et al. (2002) "Antibody Engineering at the Millennium," BioTechniques, 29, pp. 128-145.
Gillies et al. (1989) "High-level expression of chimeric antibodies using adapted cDNA variable region cassettes" J. Immunol. Methods, 125, pp. 191-202.
Goldspiel et al. (1993) "Human gene therapy," Clinical Pharmacy, 12, pp. 488-505.
Holliger et al. (1993) ""Diabodies": Small bivalent and bispecific antibody fragments," Proc. Natl. Acad. Sci. USA, 90, pp. 6444-6448.
Hoogenboom (1997) "Designing and optimizing library selection strategies for generating high-affinity antibodies" TIB Tech, 15, pp. 62-70.
Hoogenboom et al. (2000) "Natural and designer binding sites made by phage display technology," Immunology Today, 21, pp. 371-378.
Huston et al. (1988) "Protein engineering of antibody binding sites: Recovery of specific activity in an anti-digoxin single-chain Fv analogue produced in *Escherichia coli*," Proc. Natl. Acad. Sci. USA 85, pp. 5879-5883.
Johnnson et al. (1991) "Immobilization of Proteins to a Carboxymethyldextran Modified Gold Surface for Biospecific Interaction Analysis in Surface Plasmon Resonance Sensors," Anal. Biochem, 198, pp. 268-277.
Johnsson et al. (1995) "Comparison of Methods for Immobilization to Carboxymethyl Dextran Sensor Surfaces by Analysis of the Specific Activity of Monoclonal Antibodies" J. Mol. Recognit., 8, pp. 125-131.
Joliot et al. (1991) "Antennapedia homeobox peptide regulates neural morphogenesis," Proc. Natl. Acad. Sci. USA, 88, pp. 1864-1868.
Jones et al. (1986) "Replacing the complementarity determining regions in a human antibody with those from a mouse," Nature, 321, 4 pp.
Jonsson et al. (1991) "Real-Time Biospecific Interaction Analysis Using Surface Plasmon Resonance and a Sensor Chip Technology" Biotechniques, 11:5, 8 pp.
Kabat et al. (1971) "Attempts to locate complementarity determining residues in the variable positions of light and heavy chains," Ann. NY Acad. Sci., 190, pp. 382-391.
Kellermann et al. (2002) "Antibody discovery: the use of transgenic mice to generate human monoclonal antibodies for therapeutics," Current Opinion in Biotechnology, 13, pp. 593-597.
Kipriyanov et al. (1994) "Recombinant single-chain fv fragments carrying c-terminal cysteine residues: production of bivalent and biotinylated miniantibodies," Mol. Immunol., 31, pp. 1047-1058.
Kipriyanov et al. (1995) "Single-chain antibody streptavidin fusions: Tetrameric bifunctional scFv-complexes with biotin binding activity and enhanced affinity to antigen," Human Antibodies and Hybridomas, 6, pp. 93-101.
Langer (1990) "New Methods of Drug Delivery," Science, 249, 7 pp.
Levy et al. (1985) "Inhibition of Calcification of Bioprosthetic Heart Valves by Local Controlled-Release Diphosphonate," Science, 228, 3 pp.
Little et al. (2000) "Of mice and men: hybridoma and recombinant antibodies," Immunology Today, 21, pp. 364-370.
MacCallum et al. (1996), "Antibody-antigen Interactions: Contact Analysis and Binding Site Topography," J. Mol. Biol., 262(5), pp. 732-745.
Mizushima et al. (1990) "pEF-BOS, a powerful mammalian expression vector," Nucleic Acids Research, vol. 18, No. 17, 1 pg.
Morgan et al. (1993) "Human gene therapy," Ann. Rev. Biochem., 62, pp. 191-217.
Morrison et al. (1984) "Chimeric human antibody molecules: Mouse antigen-binding domains with human constant region domains," Proc. Natl. Acad. Sci., 81, pp. 851-855.
Morrison (1985) "Transfectomas Provide Novel Chimeric Antibodies," Science, 229, 6 pp.
Mulligan (1993) "The Basic Science of Gene Therapy," Science, 260, pp. 926-932.
Neuberger et al. (1984) "Recombinant antibodies possessing novel effector functions," Nature, 312, pp. 604-608.
Ning et al. (1996) "Intratumoral Radioimmunotheraphy of a Human Colon Cancer Xenograft Using a Sustained-Release Gel," Radiotherapy &Oncology, 39, pp. 179-189.
Padlan et al. (1995) "Identification of specificity-determining residues in antibodie," FASEB J., 9, pp. 133-139.
Padlan (1991) "A possible procedure for reducing the immunogenicity of antibody variable domains while preserving their ligand-binding properties," Molecular Immunology, 28, 4/5, pp. 489-498.
Poljak et al. (1994) "Production and structure of diabodies," Structure, 2, pp. 1121-1123.
Presta et al. (1993) "Humanization of an Antibody Directed Against IgE," J. Immunol., 151, 10 pp.
Jefferis (2005) "Glycosylation of Recombinant Antibody Therapeutics," Biotechnol. Prog., 21, pp. 11-16.

(56) References Cited

OTHER PUBLICATIONS

Ranger et al. (1983) "Chemical and Physical Structure of Polymers as Carriers for Controlled Release of Bioactive Agents: A Review," J. Macromol. Sci. Rev. Macromol. Chem., 23, 68 pp.

Sefton (1987) "Implantable pumps," CRC Crit. Ref. Biomed. Eng., 14(3), 20 (Abstract Only).

Shapiro et al. (2002) "DNA target motifs of somatic mutagenesis in antibody genes," Crit. Rev. Immunol., 22(3), pp. 183-200 (Abstract Only).

Song et al., 1995, "Antibody Mediated Lung Targeting of Long-Circulating Emulsions," PDA Journal of Pharmaceutical Science &Technology, 50, pp. 372-397. (Abstract Only).

Wu et al. (1991) "Delivery systems for gene therapy," Biotherapy, 3, pp. 87-95.

Wu et al. (1987) "Receptor-mediated in Vitro Gene Transformation by a Soluble DNA Carrier System," The Journal of Biological Chemistry, vol. 262, No. 10, 4 pp.

International Patent Application No. PCT/US17/63142; International Search Report and Written Opinion dated Mar. 26, 2018; 10 pgs.

Yonezawa et al. (2015), Boosting Cancer Immunotherapy with Anti-CD137 Antibody Therapy. Jul. 15, 2015, Epub Apr. 23, 2015, vol. 21, No. 14; pp. 3113-3120.

Fisher et al. (2012) "Targeting of 4-1BB by monoclonal antibody PF-05082566 enhances T-cell function and promotes anti-tumor activity," Cancer Immunol. Immunother., vol. 61, pp. 1721-1733.

Yonezawa et al. (2015) "Boosting Cancer Immunotherapy with Anti-CD137 Antibody Therapy," 2015 American Association for Cancer Research, 9 pp.

US 10,899,842 B2

4-1BB BINDING PROTEINS AND USES THEREOF

RELATED APPLICATION

This application is a 35 U.S.C. § 371 filing of International Application No. PCT/US2017/063142, filed Nov. 22, 2017, which claims priority to U.S. Patent application 62/426,074 filed Nov. 23, 2016, the entire contents of which are hereby incorporated by reference into this application.

FIELD OF THE DISCLOSURE

This disclosure relates to 4-1BB (CD137) binding proteins and their uses, especially as it relates to the treatment of various diseases.

BACKGROUND

Cancer immunotherapy enhances antitumor responses by overcoming regulatory mechanisms (check-point) of T cells. The 4-1BB (CD137) protein receptor is found on various immune cells, such as T cells, natural killer cells, and dendritic cells. 4-1BB has been shown to enhance cytotoxic T-cell responses. For review, see Yonezawa et al., Clinical Cancer Research, 21: 3113-20 (2015).

SUMMARY

This disclosure pertains to 4-1BB (CD137) binding proteins. Binding proteins of the disclosure include, but are not limited to antibodies, antigen binding portions, and other antigen binding proteins capable of binding the human 4-1BB. Further, this disclosure provides methods of making and using 4-1BB binding proteins to treat diseases such as cancers, among others.

It is disclosed here that a number of human 4-1BB antibodies that bind to human 4-1BB, stimulate and increase the number of immune cells. These antibodies may provide enhanced anti-tumor immune function by themselves. These antibodies may also work synergistically with some inhibitors of immune checkpoints (i.e. PD-1 and PD-L1 mAbs), which act to suppress T cell functions.

In one embodiment, the disclosure pertains to a binding protein capable of binding 4-1BB. In another embodiment, the binding protein binds human 4-1BB. In another embodiment, the binding protein is capable of modulating one or more biological functions of 4-1BB. In another embodiment, the binding protein is capable of neutralizing 4-1BB. In another embodiment, the binding protein does not neutralize 4-1BB. In another embodiment, the binding protein is capable of binding 4-1BB and preventing the binding of 4-1BB to its other binding target(s). In another embodiment, the binding protein is capable of acting as an agonist of 4-1BB.

One embodiment of the disclosure provides an isolated antibody, or antigen binding fragment thereof, wherein the antibody, or antigen binding fragment thereof binds human 4-1BB and inhibits the binding of the 4-1BB to its binding partner in a cell. In another embodiment, at a concentration of 50 nM 4-1BB, the EC50s for the disclosed antibodies is $10^{-6}$ M, $10^{-7}$ M, $10^{-8}$ M, $10^{-9}$ M, or $10^{-10}$ M.

In another embodiment, the binding protein is an isolated antibody. In another embodiment, the disclosure provides an isolated antibody, or antigen binding fragment thereof, wherein the antibody, or antigen binding fragment thereof binds human 4-1BB and modulates the levels and/or activities of 4-1BB. In one aspect, the antibody, or antigen binding fragment thereof inhibits the activities of 4-1BB by about 20%, 30%, 40%, 50%, 60%, 70%, 80%, 90% or 100% in a 4-1BB expressing cell after being administered to a subject in a therapeutically effective amount. In another aspect, the antibody, or antigen binding fragment thereof reduces the levels of 4-1BB by about 20%, 30%, 40%, 50%, 60%, 70%, 80%, 90% or 100% in a 4-1BB expressing cell after being administered to a subject in an therapeutically effective amount. In another aspect, the antibody, or antigen binding fragment thereof enhances the activities of 4-1BB by about 20%, 30%, 40%, 50%, 60%, 70%, 80%, 90% or 100% in a 4-1BB expressing cell after being administered to a subject in a therapeutically effective amount.

In one embodiment, the binding protein of the disclosure has an on rate constant ($k_{on}$) to 4-1BB of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, at least about $10^7$ $M^{-1}s^{-1}$, or at least about $10^8$ $M^{-1}s^{-1}$, as measured by surface plasmon resonance.

In another embodiment, the binding protein of the disclosure has an off rate constant ($k_{off}$) to 4-1BB of at most about $10^{-3}s^{-1}$, at most about $10^{-4}s^{-1}$, at most about $10^{-5}s^{-1}$, at most about $10^{-6}s^{-1}$, at most about $10^{-7}s^{-1}$, or at most about $10^{-7}s^{-1}$, as measured by surface plasmon resonance.

In another embodiment, the binding protein of the disclosure has a dissociation constant ($K_D$) to 4-1BB of at most about $10^{-7}$ M; at most about $10^{-8}$ M; at most about $10^{-9}$ M; at most about $10^{-10}$ M; at most about $10^{-11}$ M; at most about $10^{-12}$ M; or at most $10^{-13}$ M.

In one embodiment, a binding protein capable of specifically binding human 4-1BB is disclosed, wherein the binding protein comprises an antigen binding domain, and the antigen binding domain comprises six CDRs: CDR-H1, CDR-H2, CDR-H3, CDR-L1, CDR-L2, and CDR-L3, wherein CDR-H1 is selected from the group consisting of SEQ ID NO:9; SEQ ID NO:15; SEQ ID NO:21; and SEQ ID NO:27; wherein CDR-H2 is selected from the group consisting of SEQ ID NO:10; SEQ ID NO:16; SEQ ID NO:22; and SEQ ID NO:28; wherein CDR-H3 is selected from the group consisting of SEQ ID NO:11; SEQ ID NO:17; SEQ ID NO:23; and SEQ ID NO:29; CDR-L1 is selected from the group consisting of SEQ ID NO:12; SEQ ID NO:18; SEQ ID NO:24; and SEQ ID NO:30; CDR-L2 is selected from the group consisting of SEQ ID NO:13; SEQ ID NO:19; SEQ ID NO:25; and SEQ ID NO:31; and CDR-L3 is selected from the group consisting of SEQ ID NO:14; SEQ ID NO:20; SEQ ID NO:26; and SEQ ID NO:32.

In another embodiment, three of the six CDRs are selected from the group of variable domain CDR sets consisting of the following CDR sets:

VH ZW103 CDR Set
  CDR-H1: SEQ ID NO:9
  CDR-H2: SEQ ID NO:10
  CDR-H3: SEQ ID NO:11
VL ZW103 CDR Set
  CDR-L1: SEQ ID NO:12
  CDR-L2: SEQ ID NO:13
  CDR-L3: SEQ ID NO:14
VH ZW104 CDR Set
  CDR-H1: SEQ ID NO:15
  CDR-H2: SEQ ID NO:16
  CDR-H3: SEQ ID NO:17
VL ZW104 CDR Set
  CDR-L1: SEQ ID NO:18
  CDR-L2: SEQ ID NO:19
  CDR-L3: SEQ ID NO:20

VH ZW106 CDR Set
  CDR-H1: SEQ ID NO:21
  CDR-H2: SEQ ID NO:22
  CDR-H3: SEQ ID NO:23
VL ZW106 CDR Set
  CDR-L1: SEQ ID NO:24
  CDR-L2: SEQ ID NO:25
  CDR-L3: SEQ ID NO:26
VH ZW107 CDR Set
  CDR-H1: SEQ ID NO:27
  CDR-H2: SEQ ID NO:28
  CDR-H3: SEQ ID NO:29
VL ZW107 CDR Set
  CDR-L1: SEQ ID NO:30
  CDR-L2: SEQ ID NO:31
  CDR-L3: SEQ ID NO:32.

In another embodiment, the binding protein comprises at least two variable domain CDR sets selected from a group consisting of: VH ZW103 CDR Set and VL ZW103 CDR Set; VH ZW104 CDR Set and VL ZW104 CDR Set; VH ZW106 CDR Set and VL ZW106 CDR Set; VH ZW107 CDR Set and VL ZW107 CDR Set.

In another embodiment, the binding protein disclosed here further comprises human Fc region. In another embodiment, the binding protein is a human antibody or antigen binding portion thereof capable of binding 4-1BB.

In another embodiment, the binding protein disclosed here further comprises a human acceptor framework. In another embodiment, the binding protein is a CDR grafted antibody or antigen binding portion thereof capable of binding 4-1BB. In another embodiment, the CDR grafted antibody or antigen binding portion thereof comprises one or more CDRs disclosed herein. In another embodiment, the CDR grafted antibody or antigen binding portion thereof comprises a human acceptor framework.

In another embodiment, the disclosed binding protein is a humanized antibody or antigen binding portion thereof capable of binding 4-1BB. In another embodiment, the humanized antibody or antigen binding portion thereof comprise one or more CDRs disclosed above incorporated into a human antibody variable domain of a human acceptor framework. In another embodiment, the human antibody variable domain is a consensus human variable domain.

In another embodiment, the human acceptor framework comprises at least one Framework Region amino acid substitution at a key residue, wherein the key residue is selected from the group consisting of a residue adjacent to a CDR; a glycosylation site residue; a rare residue; a residue capable of interacting with human 4-1BB; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework.

In an embodiment, the binding protein is a humanized antibody or antigen binding portion thereof capable of binding 4-1BB. In another embodiment, the humanized antibody, or antigen binding portion, thereof comprises one or more CDRs disclosed herein. In another embodiment, the humanized antibody, or antigen binding portion, thereof comprises three or more CDRs disclosed herein. In another embodiment, the humanized antibody, or antigen binding portion, thereof comprises six CDRs disclosed herein.

In another embodiment, the binding protein comprises at least one variable domain having an amino acid sequence selected from the group selected from the group consisting of SEQ ID NOs.: 1-8.

In another embodiment, the binding protein comprises at least one heavy chain variable domain and at least one light chain variable domain, said heavy chain variable domain having amino acid sequence selected from the group consisting of SEQ ID NOs:1, 3, 5, 7, and 42, and said light chain variable domain having amino acid sequence selected from the group consisting of SEQ ID NOs: 2, 4, 6, 8, and 43.

In another embodiment, the binding protein may comprise two variable domains, wherein the two variable domains have amino acid sequences selected from the group consisting of the following set of variable domains:
  SEQ ID NOs:1 and 2;
  SEQ ID NOs:3 and 4;
  SEQ ID NOs:5 and 6;
  SEQ ID NOs: 7 and 8; or
  SEQ ID NOs: 42 and 43.

In one embodiment, the disclosure provides an antibody construct comprising any one of the binding proteins disclosed above and a linker polypeptide or an immunoglobulin. In another embodiment, the antibody construct is selected from the group consisting of an immunoglobulin molecule, a monoclonal antibody, a fully human antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody. In another embodiment, the antibody construct comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. In another embodiment, the disclosure provides an antibody conjugate comprising the antibody construct disclosed herein and an agent, wherein the agent is selected from the group consisting of; an immunoadhesion molecule, an imaging agent, a therapeutic agent, and a cytotoxic agent. In another embodiment, the imaging agent is selected from the group consisting of a radiolabel, an enzyme, a fluorescent label, a luminescent label, a bioluminescent label, a magnetic label, and biotin. In another embodiment, the imaging agent is a radiolabel selected from the group consisting of $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$. In another embodiment, the therapeutic or cytotoxic agent is selected from the group consisting of; an anti-metabolite, an alkylating agent, an antibiotic, a growth factor, a cytokine, an anti-angiogenic agent, an anti-mitotic agent, an anthracycline, toxin, and an apoptotic agent.

In another embodiment, the antibody construct is glycosylated. In another embodiment, the glycosylation is a human glycosylation pattern.

In another embodiment, binding protein, antibody construct or antibody conjugate disclosed herein exists as a crystal. In another embodiment, the crystal is a carrier-free pharmaceutical controlled release crystal. In another embodiment, the crystallized binding protein, crystallized antibody construct or crystallized antibody conjugate has a greater half-life in vivo than its soluble counterpart. In another embodiment, the crystallized binding protein, crystallized antibody construct or crystallized antibody conjugate retains biological activity after crystallization.

In one aspect, the binding protein may be a multispecific antibody, a dual specific antibody, and a bispecific antibody. Such antibody constructs are well known in the art, and as described and characterized in Kontermann (ed.), Bispecific Antibodies, Springer, N.Y. (2011), and Spiess et al., Mol. Immunol. 67(2):96-106 (2015). Such bispecific antibody constructs comprise one of more binding domain capable of binding 4-1BB and a second target. In one embodiment, the second target is selected from the group consisting of PD-1, PD-L1, CTLA-4, HER2/neu receptor, CSF1, MCSF, CSF2 (GM-CSF), CSF3 (GCSF), FGF2, IFN.alpha.1, IFN.beta.1, IFN.gamma., histamine and histamine receptors, IL-1.alpha., IL-1.beta., IL-2, IL-3, IL-4, IL-5, IL-6, IL-7, IL-8, IL-9, IL-10, IL-11, IL-12.alpha., IL-12.beta., IL-14, IL-15, IL-16, IL-17, IL-18, IL-19, KITLG, PDGFB, IL-2R.alpha., IL-4R, IL-5R.alpha., IL-8R.alpha., IL-8R.beta., IL-12R.beta.1, IL-12R.beta.2, GDF11R.alpha.1, GDF11R.alpha.2, IL-18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, and LTBR.

In another embodiment, the instant disclosure pertains to an isolated nucleic acid encoding any one of the binding protein, antibody construct or antibody conjugate disclosed above. A further embodiment provides a vector comprising the isolated nucleic acid disclosed above wherein said vector is selected from the group consisting of pcDNA; pTT (Durocher et al., Nucleic Acids Research 2002, Vol 30, No. 2); pTT3 (pTT with additional multiple cloning site; pEF-BOS (Mizushima, S, and Nagata, S., (1990) Nucleic acids Research Vol 18, No. 17); pBV; pJV; and pBJ.

In one embodiment, a host cell is transformed with the vector disclosed above. In another embodiment, the host cell is a prokaryotic cell. In another embodiment, the host cell is *E. coli*. In another embodiment, the host cell is a eukaryotic cell. In another embodiment, the eukaryotic cell is selected from the group consisting of protist cell, animal cell, plant cell and fungal cell. In another embodiment, the host cell is a mammalian cell including, but not limited to, CHO and COS; or a fungal cell such as *Saccharomyces cerevisiae*; or an insect cell such as Sf9.

In another embodiment, a method of producing a binding protein that binds 4-1BB is provided. The method may comprise culturing any one of the host cells disclosed above in a culture medium under conditions sufficient to produce a binding protein that binds 4-1BB. Another embodiment provides a binding protein produced according to the method disclosed above.

In another embodiment, a composition is disclosed for the release of a binding protein, wherein the composition comprises a formulation which in turn comprises a crystallized binding protein, crystallized antibody construct or crystallized antibody conjugate as disclosed above and an ingredient; and at least one polymeric carrier. In another embodiment, the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutyrate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. In another embodiment, the ingredient is selected from the group consisting of albumin, sucrose, trehalose, lactitol, gelatin, hydroxypropyl-.beta.-cyclodextrin, methoxypolyethylene glycol and polyethylene glycol.

In another embodiment, a method is disclosed for treating a mammal comprising the step of administering to the mammal an effective amount of the composition disclosed herein.

The disclosure also provides a pharmaceutical composition comprising a binding protein, antibody construct or antibody conjugate as disclosed herein and a pharmaceutically acceptable carrier. In a further embodiment, the pharmaceutical composition comprises at least one additional therapeutic agent for treating a disorder in which 4-1BB activity is detrimental. In another embodiment, the additional agent is selected from the group consisting of: therapeutic agent, imaging agent, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-IL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In one aspect, the instant disclosure provides a method for activating human 4-1BB activity comprising contacting human 4-1BB with a binding protein disclosed herein such that human 4-1BB is activated.

In another aspect, the disclosure provides a method of treating (e.g., curing, suppressing, ameliorating, delaying or preventing the onset of, or preventing recurrence or relapse of) or preventing a 4-1BB-associated disorder, in a subject. The method includes: administering to the subject a 4-1BB binding agent, e.g., an anti-4-1BB antibody or fragment thereof as described herein, in an amount sufficient to treat or prevent the 4-1BB-associated disorder. The 4-1BB binding protein, e.g., the anti-4-1BB antibody or fragment thereof, may be administered to the subject, alone or in combination with other therapeutic modalities as described herein.

In one embodiment, the subject is a mammal, e.g., a human suffering from one or more 4-1BB-associated disorders, including, e.g., respiratory disorders (e.g., asthma (e.g., allergic and nonallergic asthma), chronic obstructive pulmonary disease (COPD), and other conditions involving airway inflammation, eosinophilia, fibrosis and excess mucus production; atopic disorders (e.g., atopic dermatitis and allergic rhinitis); inflammatory and/or autoimmune conditions of, the skin, gastrointestinal organs (e.g., inflammatory bowel diseases (IBD), such as ulcerative colitis and/or Crohn's disease), and liver (e.g., cirrhosis, fibrosis); scleroderma; tumors or cancers, e.g., Hodgkin's lymphoma as described herein. Accordingly, the disclosure includes the use of a 4-1BB binding agent (such as an anti-4-1BB antibody or fragment thereof described herein) for a treatment described herein and the use of a 4-1BB complex agent (such as an anti-4-1BB antibody or fragment thereof described herein) for preparing a medicament for a treatment described herein. Examples of 4-1BB-associated disorders include, but are not limited to, cancers, as described herein.

In another aspect, this application provides a method for detecting the presence of 4-1BB in a sample in vitro (e.g., a biological sample, such as serum, plasma, tissue, and biopsy). The subject method can be used to diagnose a disorder. The method includes: (i) contacting the sample or a control sample with the anti-4-1BB antibody or fragment thereof as described herein; and (ii) detecting formation of a complex between the anti-4-1BB antibody or fragment thereof, and the sample or the control sample, wherein a statistically significant change in the formation of the complex in the sample relative to the control sample is indicative of the presence of the 4-1BB in the sample.

In another aspect, this application provides a method for detecting the presence of 4-1BB in vivo (e.g., in viva imaging in a subject). The subject method can be used to diagnose a disorder, e.g., a 4-1BB-associated disorder. The method includes: (i) administering the anti-4-1BB antibody or fragment thereof as described herein to a subject or a control subject under conditions that allow binding of the antibody or fragment to 4-1BB; and (ii) detecting formation of a complex between the antibody or fragment and 4-1BB, wherein a statistically significant change in the formation of the complex in the subject relative to the control subject is indicative of the presence of 4-1BB.

In another aspect, the binding proteins of the disclosure may be useful for treating a disorder selected from the group consisting of Thalassemia, beta thalassemia, anemia, iron deficiency anemia, plummer-vinson syndrome, pernicious anemia, megaloblastic anemia, protein deficiency anemia, scurvy, acanthocytosis, alpha-thalassemia, aplastic anemia, congenital dyserythropoietic anemia, hemolytic anemia fanconi anemia, hereditary sperocytosis, hereditary elliptocytosis, hereditary pyropoilikocytosis cold hemagglutinin disease, hemolytic uremic syndrome, hyperanemia, ineffective erythropesis, cacrocytic anemia, myelophthisic anemia, neuroacanthocytosis, chorea, acanthoscytosis, pyruvate kinase deficiency, sickle cell disease, thriosephophosphate isomerase deficiency, arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasulitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), H is bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multi system disorder, mixed connective tissue disease, monoclonal gammopathy, multiple myeloma, multiple systems degenerations (Mencel Dejerine-Thomas Shi-Drager and Machado-Joseph), myasthenia gravis, *Mycobacterium avium* intracellulare, *Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, Acute coronary syndromes, Acute Idiopathic Polyneuritis, Acute Inflammatory Demyelinating Polyradiculoneuropathy, Acute ischemia, Adult Still's Disease, Alopecia greata, Anaphylaxis, Anti-Phospholipid Antibody Syndrome, Aplastic anemia, Arteriosclerosis, Atopic eczema, Atopic dermatitis, Autoimmune dermatitis, Autoimmune disorder associated with Streptococcus infection, Autoimmune Enteropathy, Autoimmune hearingloss, Autoimmune Lymphoproliferative Syndrome (ALPS), Autoimmune myocarditis, Autoimmune premature ovarian failure, Blepharitis, Bronchiectasis, Bullous pemphigoid, Cardiovascular Disease, Catastrophic Antiphospholipid Syndrome, Celiac Disease, Cervical Spondylosis, Chronic ischemia, Cicatricial pemphigoid, Clinically isolated Syndrome (CIS) with Risk for Multiple Sclerosis, Conjunctivitis, Childhood Onset Psychiatric Disorder, Chronic obstructive pulmonary disease (COPD), Dacryocystitis, dermatomyositis, Diabetic retinopathy, Diabetes mellitus, Disk herniation, Disk prolaps, Drug induced immune hemolytic anemia, Endocarditis, Endometriosis, endophthalmitis, Episcleritis, Erythema multiforme, erythema multiforme major, Gestational pemphigoid, Guillain-Barre Syndrome (GBS), Hay Fever, Hughes Syndrome, Idiopathic Parkinson's Disease, idiopathic interstitial pneumonia, IgE-mediated Allergy, Immune hemolytic anemia, Inclusion Body Myositis, Infectious ocular inflammatory disease, Inflammatory demyelinating disease, Inflammatory heart disease, Inflammatory kidney disease, IPF/UIP, Iritis, Keratitis, Keratojuntivitis sicca, Kussmaul disease or Kussmaul-Meier Disease, Landry's Paralysis, Langerhan's Cell Histiocytosis, Livedo reticularis, Macular Degeneration, Microscopic Polyangiitis, Morbus Bechterev, Motor Neuron Disorders, Mucous membrane pemphigoid, Multiple Organ failure, Myasthenia Gravis, Myelodysplastic Syndrome, Myocarditis, Nerve Root Disorders, Neuropathy, Non-A Non-B Hepatitis, Optic Neuritis, Osteolysis, Pauciarticular JRA, peripheral artery occlusive disease (PAOD), peripheral vascular disease (PVD), peripheral artery disease (PAD), Phlebitis, Polyarteritis nodosa (or periarteritis nodosa), Polychondritis, Polymyalgia Rheumatica, Poliosis, Polyarticular JRA, Polyendocrine Deficiency Syndrome, Polymyositis, polymyalgia rheumatica (PMR), Post-Pump Syndrome, primary parkinsonism, Prostatitis, Pure red cell aplasia, Primary Adrenal Insufficiency, Recurrent Neuromyelitis Optica, Restenosis, Rheumatic heart disease, SAPHO (synovitis, acne, pustulosis, hyperostosis, and osteitis), Scleroderma, Secondary Amyloidosis, Shock lung, Scleritis, Sciatica, Secondary Adrenal Insufficiency, Silicone associated connective tissue disease, Sneddon-Wilkinson Dermatosis, spondilitis ankylosans, Stevens-Johnson Syndrome (SJS), Systemic inflammatory response syndrome, Temporal arteritis, toxoplasmic retinitis, toxic epidermal necrolysis, Transverse myelitis, TRAPS (Tumor Necrosis Factor Receptor, Type 1 allergic reaction, Type II Diabetes, Urticaria, Usual interstitial pneumonia (UIP), Vasculitis, Vernal conjunctivitis, viral retinitis, Vogt-Koyanagi-Harada syndrome (VKH syndrome), Wet macular degeneration, and Wound healing.

In another aspect, the binding proteins of the disclosure may be useful for treating a disorder selected from the group consisting of Acute Lymphoblastic Leukemia, Acute Myeloid Leukemia, Adrenocortical Carcinoma, Anal Cancer, Appendix Cancer, Cerebellar Astrocytoma, Cerebral Astrocytoma, Basal Cell Carcinoma, Bile Duct Cancer, Extrahepatic, Bladder Cancer, Bone Cancer, Osteosarcoma/Malignant Fibrous Histiocytoma Brain Stem Glioma, Brain Tumor, Brain Stem Glioma, Cerebral strocytoma/Malignant Glioma, Ependymoma, Medulloblastoma, Supratentorial Primitive Neuroectodermal Tumors, Visual Pathway and Hypothalamic Glioma, Breast Cancer, Bronchial Adenomas/Carcinoids, Carcinoid Tumor, Carcinoid Tumor, Gastrointestinal Carcinoma of Unknown Primary, Central Nervous System Lymphoma, Primary Cerebellar Astrocytoma, Cervical Cancer, Chronic Lymphocytic Leukemia, Chronic Myelogenous Leukemia Chronic Myeloproliferative Disorders, Colon Cancer, Colorectal Cancer, Cutaneous T-Cell Lymphoma, Endometrial Cancer, Ependymoma, Esophageal Cancer, Ewing Family of Tumors, Extracranial Germ Cell Tumor, Extragonadal Germ Cell Tumor, Extrahepatic Bile Duct Cancer, Eye Cancer, Intraocular Melanoma Retinoblastoma, Gallbladder Cancer, Gastric (Stomach) Cancer, Gastrointestinal Carcinoid Tumor, Gastrointestinal Stromal Tumor (GIST), Extracranial Germ Cell Tumor, Extragonadal Germ Cell Tumor, Ovarian Germ Cell Tumor, Gestational Trophoblastic Tumor, Glioma, Brain Stem Glioma, Cerebral Astrocytoma Glioma, Childhood Visual Pathway and Hypothalamic Glioma, Hairy Cell Leukemia, Head and Neck Cancer, Hepatocellular (Liver) Cancer, Hodgkin Lymphoma, Hypopharyngeal Cancer, Intraocular Melanoma, Islet Cell Carcinoma (Endocrine Pancreas), Kaposi Sarcoma, Kidney (Renal Cell) Cancer, Laryngeal Cancer, Acute Lymphoblastic Leukemia, Acute Myeloid Leukemia, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Burkitt Lymphoma, Cutaneous T-Cell Lymphoma, Hodgkin Lymphoma, Non-Hodgkin Lymphoma, Primary Central Nervous System Lymphoma, Waldenstrom Macroglobulinemia, Malignant Fibrous Histiocytoma of Bone/Osteosarcoma, Medulloblastoma, Melanoma, Intraocular (Eye) Melanoma, Merkel Cell Carcinoma, Malignant Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic Myeloid Leukemia, Multiple Myeloma, Myeloproliferative Disorders, Nasal Cavity and Paranasal Sinus Cancer, Nasopharyngeal Cancer, Neuroblastoma, Oral Cancer, Oral Cavity Cancer, Lip and Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Islet Cell Pancreatic Cancer, Paranasal Sinus and Nasal Cavity Cancer, Parathyroid Cancer, Penile Cancer, Pharyngeal Cancer, Pheochromocytoma, Pineoblastoma and Supratentorial Primitive Neuroectodermal Tumors, Pituitary Tumor, Plasma Cell Neoplasmi/Multiple Myeloma, Pleuropulmonary Blastoma, Prostate Cancer, Rectal Cancer, Renal Cell (Kidney) Cancer, Renal Pelvis and Ureter, Transitional Cell Cancer, Retinoblastoma, Salivary Gland Cancer, Sarcoma, Ewing Family of Tumors, Kaposi Sarcoma, Soft Tissue Sarcoma, Uterine Sarcoma, Sezary Syndrome, Skin Cancer (Nonmelanoma), Skin Cancer (Melanoma), Merkel Cell Skin Carcinoma, Small Intestine Cancer, Squamous Cell Carcinoma, Metastatic Squamous Neck Cancer with Occult Primary, Stomach (Gastric) Cancer, Supratentorial Primitive Neuroectodermal Tumors, Cutaneous T-Cell Lymphoma, Testicular Cancer, Throat Cancer, Thymoma, Thymoma and Thymic Carcinoma, Thyroid Cancer, Transitional Cell Cancer of the Renal Pelvis and Ureter, Gestational Trophoblastic Tumor, Ureter and Renal Pelvis, Transitional Cell Cancer, Urethral Cancer, Uterine Cancer, Endometrial Uterine Sarcoma, Vaginal Cancer, Visual Pathway and Hypothalamic Glioma, Vulvar Cancer, Waldenstrom Macroglobulinemia, and Wilms Tumor.

In another aspect the disclosure provides a method of treating a patient suffering from a disorder in which human 4-1BB activity is implicated, comprising the step of administering any one of the binding proteins disclosed above before, concurrent, or after the administration of a second agent, as discussed herein. In an embodiment, the additional therapeutic agent that may be coadministered and/or coformulated with one or more 4-1BB binding proteins, include, but are not limited to, one or more of: inhaled steroids; oral steroids; beta-agonists, e.g., short-acting or long-acting beta-agonists; antagonists of leukotrienes or leukotriene receptors; combination drugs such as ADVAIR; IgE inhibitors, e.g., anti-IgE antibodies (e.g., XOLAIR); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-4-1BB antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others. Additional second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors; IL-1 receptor antagonists, anti-IL-1.beta. monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adensosine agonists, antithrombotic agents, complement inhibitors, adrenergic agents, IRAK, NIK, IKK, p38, MAP kinase inhibitors, IL-1.beta, converting enzyme inhibitors, TNF converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, and TGF-beta.

In another embodiment, the pharmaceutical compositions disclosed herein are administered to the subject by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

In another embodiment, the disclosure provides at least one 4-1BB anti-idiotype antibody to at least one binding protein disclosed herein. The anti-4-1BB idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present disclosure.

DETAILED DESCRIPTION

Figure 1:
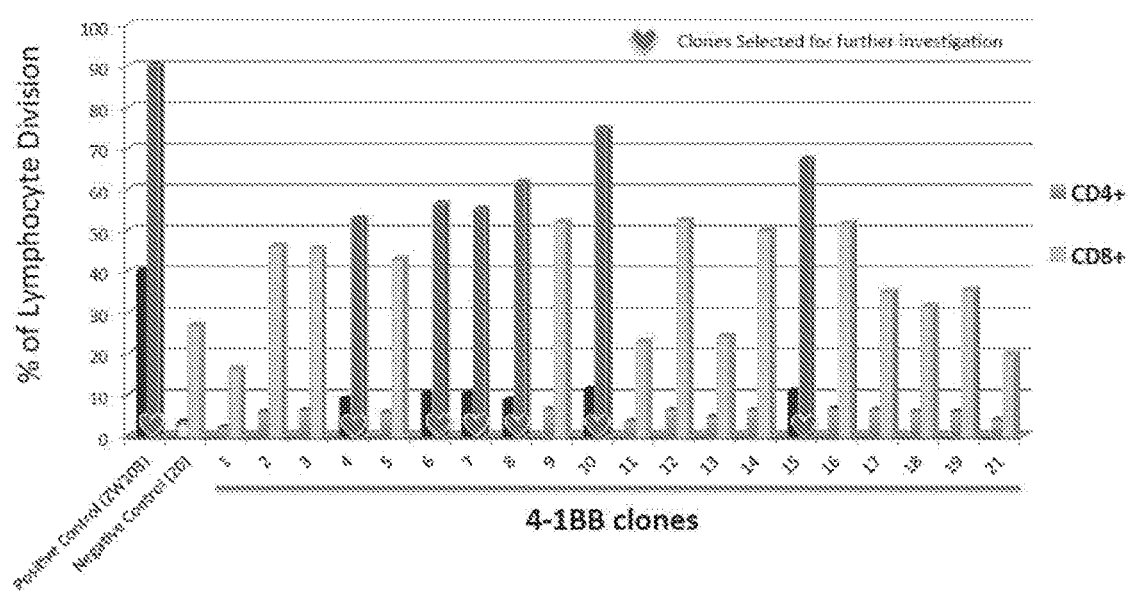
FIG. 1 shows that ZW103 (other clones show similar effect (data not shown)) are capable of expanding CD4+ T cell or CD8+ T cell in conjunction with one or more co-stimulator(s).

This disclosure pertains to 4-1BB binding proteins, and more particularly to anti-4-1BB antibodies, or antigen-binding portions thereof, that bind 4-1BB. Various aspects of the disclosure relate to antibodies and antibody fragments, and pharmaceutical compositions thereof, as well as nucleic acids, recombinant expression vectors and host cells for making such antibodies and fragments. Methods of using the antibodies of the disclosure to detect human 4-1BB, to modulate human 4-1BB activities and/or levels, either in vitro or in vivo are also disclosed.

Unless otherwise defined herein, scientific and technical terms used in connection with the present disclosure shall have the meanings that are commonly understood by those of ordinary skill in the art. The meaning and scope of the terms are clear, however, in the event of any latent ambiguity, definitions provided herein take precedent over any dictionary or extrinsic definition. Further, unless otherwise required by context, singular terms shall include pluralities and plural terms shall include the singular. In this disclosure, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present disclosure unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present disclosure may be more readily understood, select terms are defined below.

The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

"Biological activity" or "activity" of a protein, as used herein, refers to all inherent biological properties of the protein.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., 4-1BB). It has been shown that the antigen-binding function of an antibody can be performed by fragments of a full-length antibody. Such antibody embodiments may also be bispecific, dual specific, or multi-specific formats; specifically binding to two or more different antigens. Multispecific, dual specific, and bispecific antibody constructs are well known in the art and described and characterized in Kontermann (ed.), Bispecific Antibodies, Springer, N.Y. (2011), and Spiess et al., Mol. Immunol. 67(2):96-106 (2015).

Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more antigen binding portions of the disclosure linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences and their functional variations are known in the art.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds human 4-1BB is substantially free of antibodies that specifically bind antigens other than h4-1BB). An isolated antibody that specifically binds h4-1BB may, however, have cross-reactivity to other antigens, such as 4-1BB molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human 4-1BB which can be generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti human 4-1BB antibodies and antigen binding portions are provided. Such antibodies were generated by obtaining murine anti-h4-1BB monoclonal antibodies using traditional hybridoma technology followed by humanization using in vitro genetic engineering, such as those disclosed in Kasaian et al PCT publication No. WO 2005/123126 A2.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242).

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In an embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment, the acceptor sequences known in the art may be used in the antibodies disclosed herein.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In another embodiment, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

In one embodiment, the framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In another embodiment, such mutations, however, will not be extensive. Usually, at least 80%, 85%, 90%, and or 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. In another embodiment, if two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. In another embodiment, a multivalent binding protein may be engineered to have three or more antigen binding sites, and is generally not a naturally occurring antibody.

The term "multispecific binding protein" refers to a binding protein capable of binding two or more related or unrelated targets. As referenced earlier, such antibody constructs are well known in the art, and as described and characterized in Kontermann (ed.), Bispecific Antibodies, Springer, N.Y. (2011), and Spiess et al., Mol. Immunol. 67(2):96-106 (2015). Such bispecific antibody constructs include but are not limited to those commonly known as, Minibodies, Nanobodies, Diabodies, Bites, Duobodies, Tandemabs, Knobs-into-holes Igs, DAFs, CT-Igs, DutamAbs, DVD-Igs, CoDVD-Igs, CoDV-Igs, FIT-Igs, CrossmAbs, CrossfAbs, SEEDbodies, TriomAbs, LUZ-Ys, Zybodies. Multispecific binding proteins as used herein, are binding proteins that comprise two or more antigen binding sites and are tetravalent or multivalent binding proteins. Such DVDs may be monospecific, i.e. capable of binding one antigen or multispecific, i.e. capable of binding two or more antigens.

As used herein, the term "neutralizing" refers to neutralization of the biological activity of a target protein when a binding protein specifically binds the target protein. For example, a neutralizing 4-1BB binding protein may be a neutralizing antibody whose binding to 4-1BB results in inhibition of a biological activity of 4-1BB. In one embodiment, the neutralizing binding protein binds 4-1BB and reduces a biologically activity of 4-1BB by at least about 20%, 40%, 60%, 80%, 85% or more. Inhibition of a biological activity of 4-1BB by a neutralizing binding protein can be assessed by measuring one or more indicators of the biological activity of 4-1BB well known in the art. In another embodiment, the 4-1BB binding protein of this disclosure is not a neutralizing antibody.

The term "activity" includes activities such as the binding specificity/affinity of an antibody for an antigen.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_D$", as used herein, is intended to refer to the dissociation constant of a particular antibody-antigen interaction as is known in the art.

The term "labeled binding protein" as used herein, refers to a protein with a label incorporated that provides for the identification of the binding protein. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. In another embodiment, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA.

The term "isolated polynucleotide" as used herein shall mean a polynucleotide (e.g., of genomic, cDNA, or synthetic origin, or some combination thereof) that, by virtue of its origin, is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present disclosure may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., WO 2007/014162 incorporated herein by reference).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell.

Because certain modifications may occur in succeeding generations due to either mutation or environmental influences, such progeny may not, in fact, be identical to the parent cell, but are still included within the scope of the term "host cell" as used herein. In another embodiment, host cells include prokaryotic and eukaryotic cells selected from any of the Kingdoms of life. In another embodiment, eukaryotic cells include protist, fungal, plant and animal cells. In another embodiment, host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of 4-1BB). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of 4-1BB). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO0183525.

The term "agonist", as used herein, refers to a modulator that, when contacted with a molecule of interest, causes an increase in the magnitude of a certain activity or function of the molecule compared to the magnitude of the activity or function observed in the absence of the agonist. Agonists of 4-1BB may include, but are not limited to, proteins (e.g., Ab), nucleic acids, carbohydrates, or any other molecules, which bind to 4-1BB. In one embodiment, the 4-1BB binding proteins of this disclosure are 4-1BB agonists.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of 4-1BB. Antagonists and inhibitors of 4-1BB may include, but are not limited to, proteins (e.g., Ab), nucleic acids, carbohydrates, or any other molecules that bind to 4-1BB. In another embodiment, the 4-1BB binding proteins of this disclosure are not 4-1BB antagonists.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Binding Proteins that Bind Human 4-1BB

One aspect of the present disclosure provides antibodies, or portions thereof, that are isolated antibodies. One aspect of the present disclosure provides isolated monoclonal antibodies, or antigen-binding portions thereof, that bind to 4-1BB with high affinity, a slow off rate and high neutralizing capacity. Another aspect of the disclosure provides antibodies that specifically bind human 4-1BB (h4-1BB). Another aspect of the disclosure provides fully human antibodies that bind 4-1BB. Another aspect of the disclosure provides murine antibodies that bind 4-1BB. Another aspect of the disclosure provides chimeric antibodies that bind 4-1BB. Another aspect of the disclosure provides humanized antibodies, or antigen-binding portions thereof, that bind 4-1BB. In one embodiment, antibodies, or portions thereof, specifically bind h4-1BB.

A. Method of Making Anti-4-1BB Antibodies

Antibodies of the present disclosure may be made by any of a number of techniques known in the art, as illustrated in the Examples.

1. 4-1BB Binding Proteins

Table 1 is an abbreviated sequence list of candidate anti-4-1BB antibody clones.

TABLE 1

List of Amino Acid Sequences of VH and VL regions of mouse monoclonal antibodies against human 4-1BB

| clone | polypeptide region | Amino acid sequence | SEQ ID No. |
|---|---|---|---|
| ZW103 | VH | QVQLQQSGAELVRPGVSVKISCKGSGYTFTDYAMHW VKQSHVKSLEWIGGISTYNGDASYNQKFKGKATMTV DKSSRTAYMELVRLTSEDSAIYYCAPSNYGYAMDYW GQGTSVTVSS | 1 |
| ZW103 | VL | DIVMSQSPSSLAVSVGEKVSVSCKSSQSLLYSSNQK NYLAWYQQKPGQSPKLLIYWASTRESGVPDRFTGSG SGTDFTLTISSVKAEDLAVYYCQQYLSYPWTFGGGT KLEIN | 2 |
| ZW104 | VH | QVQLQQSGAELARPGASVKMSCKASGYIFTTYAMHW VKQRPGQGLEWIGYINPTTVYTIYNQKFKDKATLTA DKSSSTAYMQLSSLTSEDSAVYYCARLGGHWYFDVW GAGTTVTVSS | 3 |
| ZW104 | VL | DIVLTQSPASLAVSLGQRATISCRASESVDNYGISF MNWFQQKPGQPPKLLIYSASNQGSGVPARFSGSGSG TDFSLNIHPMEEDDTAMYFCQQSKEVPWTFGGGTKL EIK | 4 |
| ZW106 | VH | QVQLQQPESELVRPGGSVKLSCKASGYTFTSYWMDW VKQRHGQGLEWIGNIYPDSGGTNYAEKFKSKATLTV DTSSSTAYMHLSSLTSEDSAVYYCTREEALGGYYEL TYWGQGTLVTVSA | 5 |
| ZW106 | VL | DIVLTQSPASLPVSLGQRATISCRASQSVSTSSYSY MHWYQQKPGQPPKLLIKYASNLESGVPARFSGSGSG TDFTLNIHPVEEEDTATYYCQHSWEIPYTFGGGTKL EIE | 6 |
| ZW107 | VH | QVQLQQSGAELVRPGTSVKISCKASGYAFTNYWLGW VKQRPGHGLEWIGDIYPGNGNNYYSEKFKDKATLTA DKSSSTVYIRLSSLTSEDSAVYFCARHGSFRSAMDY WGQGTSVTVSS | 7 |
| ZW107 | VL | DIQMTQSPASPSASVGETVTITCRASENIYSYLAWY QQKQGKSPQLLVYNAKTLADGVPSRFSGSGSGTQFS LKINSLQPEDFGSYYCQHHYGTPPTFGGGTKLEIK | 8 |

The CDR sequences of each clone are listed in Tables 2-5 below.

TABLE 2

CDR sequences of Clone ZW103

| Clone | Amino acid sequence | SEQ ID No. |
|---|---|---|
| CDRH1 | DYAMH | 9 |
| CDRH2 | GISTYNGDASYNQKFKG | 10 |
| CDRH3 | SNYGYAMDY | 11 |
| CDRL1 | KSSQSLLYSSNQKNYLA | 12 |
| CDRL2 | WASTRES | 13 |
| CDRL3 | QQYLSYPWT | 14 |

TABLE 3

CDR sequences of Clone ZW104

| Clone | Amino acid sequence | SEQ ID No. |
|---|---|---|
| CDRH1 | TYAMH | 15 |
| CDRH2 | YINPTTVYTIYNQKFKD | 16 |
| CDRH3 | LGGHWYFDV | 17 |
| CDRL1 | RASESVDNYGISFMN | 18 |
| CDRL2 | SASNQGS | 19 |
| CDRL3 | QQSKEVPWT | 20 |

TABLE 4

CDR sequences of Clone ZW106

| Clone | Amino acid sequence | SEQ ID No. |
|---|---|---|
| CDRH1 | SYWMD | 21 |
| CDRH2 | NIYPDSGGTNYAEKFKS | 22 |
| CDRH3 | EEALGGYYELTY | 23 |
| CDRL1 | RASQSVSTSSYSYMH | 24 |

TABLE 4-continued

CDR sequences of Clone ZW106

| Clone | Amino acid sequence | SEQ ID No. |
|---|---|---|
| CDRL2 | YASNLES | 25 |
| CDRL3 | QHSWEIPYT | 26 |

TABLE 5

CDR sequences of Clone ZW107

| Clone | Amino acid sequence | SEQ ID No. |
|---|---|---|
| CDRH1 | NYWLG | 27 |
| CDRH2 | DIYPGNGNNYYSEKFKD | 28 |
| CDRH3 | HGSFRSAMDY | 29 |
| CDRL1 | RASENIYSYLA | 30 |
| CDRL2 | NAKTLAD | 31 |
| CDRL3 | QHHYGTPPT | 32 |

Table 6 shows the heavy chain sequence including the leader sequence of ZW103-107 clones.

TABLE 7

List of Amino Acid Sequences of HC and LC of candidate antibody clones

| clone | polypeptide region | Amino acid sequence | SEQ ID No. |
|---|---|---|---|
| ZW103 | HC | MGWSCIIVFLVATATGVHSQVQLQQSGAELVRPGVS VKISCKGSGYTFTDYAMHWVKQSHVKSLEWIGGIST YNGDASYNQKFKGKATMTVDKSSRTAYMELVRLTSE DSAIYYCAPSNYGYAMDYWGQGTSVTVSS | 33 |
| ZW103 | LC | MDSQAQVLMLLLLWVSGTCGDIVMSQSPSSLAVSVG EKVSVSCKSSQSLLYSSNQKNYLAWYQQKPGQSPKL LIYWASTRESGVPDRFTGSGSGTDFTLTISSVKAED LAVYYCQQYLSYPWTFGGGTKLEIN | 34 |
| ZW104 | HC | MERHWIFLLLLSVTAGVHSQVQLQQSGAELARPGAS VKMSCKASGYIFTTYAMHWVKQRPGQGLEWIGYINP TTVYTIYNQKFKDKATLTADKSSSTAYMQLSSLTSE vDSAVYYCARLGGHWYFDVWGAGTTVTVSS | 35 |
| ZW104 | LC | MEKDTLLLWVLLLWVPGSTGDIVLTQSPASLAVSLG QRATISCRASESVDNYGISFMNWFQQKPGQPPKLLI YSASNQGSGVPARFSGSGSGTDFSLNIHPMEEDDTA MYFCQQSKEVPWTFGGGTKLEIK | 36 |
| ZW106 | HC | MGWSCIILFLVATATGVHSQVQLQQPESELVRPGGS VKLSCKASGYTFTSYWMDWVKQRHGQGLEWIGNIYP DSGGTNYAEKFKSKATLTVDTSSSTAYMHLSSLTSE DSAVYYCTREEALGGYYELTYWGQGTLVTVSA | 37 |
| ZW106 | LC | METDTLLLWVLLLWVPGSTGDIVLTQSPASLPVSLG QRATISCRASQSVSTSSYSYMHWYQQKPGQPPKLLI KYASNLESGVPARFSGSGSGTDFTLNIHPVEEEDTA TYYCQHSWEIPYTFGGGTKLEIE | 38 |
| ZW107 | HC | MEWSGVFIFLLSVTAGVHSQVQLQQSGAELVRPGTS VKISCKASGYAFTNYWLGWVKQRPGHGLEWIGDIYP GNGNNYYSEKFKDKATLTADKSSSTVYIRLSSLTSE DSAVYFCARHGSFRSAMDYWGQGTSVTVSS | 39 |
| ZW107 | LC | MSVPTQVLGLLLLWLTGARCDIQMTQSPASPSASVG ETVTITCRASENIYSYLAWYQQKQGKSPQLLVYNAK TLADGVPSRFSGSGSGTQFSLKINSLQPEDFGSYYC QHHYGTPPTFGGGTKLEIK | 40 |

The foregoing isolated anti-4-1BB antibody CDR sequences establish a novel family and motif of 4-1BB binding proteins, isolated in accordance with this disclosure, and comprising polypeptides that include the sequences listed in Tables 1-6.

Humanized anti-4-1BB antibodies have also been generated. By way of example, Table 7 shows sequences of humanized ZW106.

TABLE 7

List of Amino Acid Sequences of VH and VL of humanized ZW106-2

| clone | polypeptide region | Amino acid sequence | SEQ ID No. |
|---|---|---|---|
| ZW106-2 | VH | EVQLVQSGAEVKKPGASVKVSCKASGYTFTSYWMDW VRQAPGQGLEWMGNIYPDSGGTNYAEKFKSRVTLTV DTSISTAYMELSRLRSDDTAVYYCAREEALGGYYEL TYWGQGTLVTVSS | 42 |
| ZW106-2 | VL | DIVMTQSPDSLAVSLGERATINCRASQSVSTSSYSY MHWYQQKPGQPPKLLIKYASNLESGVPDRFSGSGSG TDFTLTISSLQAEDVAVYYCQHSWEIPYTFGGGTKV EIK | 43 |
| ZW106-2 | CH | ASTKGPSVFPLAPCSRSTSESTAALGCLVKDYFPEP VTVSWNSGALTSGVHTFPAVLQSSGLYSLSSVVTVP SSSLGTKTYTCNVDHKPSNTKVDKRVESKYGPPCPP CPAPEFLGGPSVFLFPPKPKDTLMISRTPEVTCVVV DVSQEDPEVQFNWYVDGVEVHNAKTKPREEQFNSTY RVVSVLTVLHQDWLNGKEYKCKVSNKGLPSSIEKTI SKAKGQPREPQVYTLPPSQEEMTKNQVSLTCLVKGF YPSDIAVEWESNGQPENNYKTTPPVLDSDGSFFLYS RLTVDKSRWQEGNVFSCSVMHEALHNHYTQKSLSLS LGK | 44 |
| ZW106-2 | CL | RTVAAPSVFIFPPSDEQLKSGTASVVCLLNNFYPRE AKVQWKVDNALQSGNSQESVTEQDSKDSTYSLSSTL TLSKADYEKHKVYACEVTHQGLSSPVTKSFNRGEC | 45 |

2. Anti 4-1BB Chimeric Antibodies

A chimeric antibody is a molecule in which different portions of the antibody are derived from different origins or animal species. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the disclosure are produced by inserting the CDRs of the anti-4-1BB binding proteins described herein with a human IgG1 constant region.

3. Anti 4-1BB Humanized Antibodies

Humanized antibodies are antibody molecules from non-human species antibody that bind the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.edu/. about.pedro/research_tools.html; www.mgen.uni-heidelberg.de/SD/IT/IT.html; www.whfreeman.com/immunology/CH-05/kuby05.htm; www.library.thinkquest.org/12429/Immune/Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/Immunology.html.www.immunologylink.com/; pathbox.wustl.edu/. about.hcenter/index.-html; www.biotech.ufl.edu/about.hcl/; www.pebio.com/pa/340913/340913.html-; www.nal.usda. gov/awic/pubs/antibody/; www.m.ehime-u.acjp/.about.yasuhito-/Elisa.html; www.biodesign.con/table.asp; www.icnet.uk/axp/facs/davies/links.html; www.biotech.ufl.edu/.about.fccl/protocol.html; www.isac-net.org/sites_ geo.html; aximtl.imt.uni-marburg.de/. about.rek/AEP-Start.html; baserv.uci.kun.nl/aboutjraats/linksl.html; www.recab.uni-hd.de/immuno.bme.nwu.edu/; www.mrc-cpe.cam.ac.uk/imt-doc/public/INTRO.html; www.ibt.unam.mx/vir/V_mice.html; imgt.cnusc.fr:8104/; www.biochem.uct.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path. cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.abo-ut.fmolina/Web-pages/Pept/spottech.html; www.jerini.de/fr roducts.htm; www.patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, or improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994), Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817, 483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

In one embodiment, anti-4-1BB binding proteins of the present disclosure may exhibit a high capacity to reduce or to enhance 4-1BB activity, e.g., as assessed by any one of several in vitro and in vivo assays known in the art.

In certain embodiments, the antibody comprises a heavy chain constant region, such as an IgG1, IgG2, IgG3, IgG4, IgA, IgE, IgM or IgD constant region. In another embodiment, the heavy chain constant region is an IgG1 heavy chain constant region or an IgG4 heavy chain constant region. Furthermore, the antibody can comprise a light chain constant region, either a kappa light chain constant region or a lambda light chain constant region. In another embodiment, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the disclosure is derivatized or linked to another functional molecule (e.g., another peptide or protein). For example, a labeled binding protein of the disclosure can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the disclosure may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the disclosure provides a crystallized binding protein. In another embodiment, the disclosure relates to crystals of whole anti-4-1BB antibodies and fragments thereof as disclosed herein, and formulations and compositions comprising such crystals. In another embodiment, the crystallized binding protein has a greater half-life in vivo than the soluble counterpart of the binding protein. In another embodiment the binding protein retains biological activity after crystallization.

Crystallized binding protein of the disclosure may be produced according methods known in the art and as disclosed in WO 02072636, incorporated herein by reference.

Another embodiment of the disclosure provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, Biotechnol. Prog. 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present disclosure.

In another embodiment, the glycosylation of the antibody or antigen-binding portion of the disclosure is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified antibody of the disclosure can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the disclosure may include, but are not limited to, glucose, galactose, mannose, fucose, n-acetylglucosamine and sialic acid. In another embodiment, the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent applications 20040018590 and 20020137134 and PCT publication WO2005100584 A2).

In addition to the binding proteins, the present disclosure is also directed to an anti-idiotypic (anti-Id) antibody specific for such binding proteins of the disclosure. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. In another embodiment, the protein having a particularly selected novel glycosylation pattern exhibits improved or altered biological properties.

The disclosure also provides pharmaceutical compositions comprising a binding protein, antibody, or antigen-binding portion thereof, of the disclosure and a pharmaceutically acceptable carrier. The pharmaceutical compositions comprising antibodies of the disclosure are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the disclosure. In another embodiment, the pharmaceutical composition comprises one or more antibodies of the disclosure and one or more prophylactic or therapeutic agents other than antibodies of the disclosure for treating a disorder in which 4-1BB activity is too high or too low. In one embodiment, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the disclosure can be incorporated into pharmaceutical compositions suitable for administration to a subject. Typically, the pharmaceutical composition comprises an antibody or antibody portion of the disclosure and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the disclosure or the combination of one or more antibodies of the disclosure and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the disclosure include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the disclosure, combination therapy, or a composition of the disclosure is administered using Alkermes AIR® pulmonary drug delivery technology (Alkermes, Inc., Cambridge, Mass.). In a specific embodiment, prophylactic or therapeutic agents of the disclosure are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the disclosure locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices, or collagen matrices. In one embodiment, an effective amount of one or more antibodies of the disclosure antagonists is administered locally to the affected area to a subject to prevent, treat, manage, and/or ameliorate a disorder or a symptom thereof. In another embodiment, an effective amount of one or more antibodies of the disclosure is administered locally to the affected area in combination with an effective amount of one or more therapies (e.g., one or more prophylactic or therapeutic agents) other than an antibody of the disclosure of a subject to prevent, treat, manage, and/or ameliorate a disorder or one or more symptoms thereof.

In another embodiment, the prophylactic or therapeutic agent of the disclosure can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the disclosure. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Intl. Symp. Control. Rel. Bioact. Mater. 24:853-854, and Lam et al., 1997, "Microencapsulation of Recombinant Humanized Monoclonal Antibody for Local Delivery," Proc. Intl. Symp.

Control Rel. Bioact. Mater. 24:759-760, each of which is incorporated herein by reference in their entireties.

In a specific embodiment, where the composition of the disclosure is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the disclosure is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the disclosure are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semisolid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the disclosure comprises intranasal administration of a composition, the composition can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the disclosure comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the disclosure may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the disclosure, combination therapy, and/or composition of the disclosure is administered using Alkermes AIR® pulmonary drug delivery technology (Alkermes, Inc., Cambridge, Mass.).

The method of the disclosure may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the disclosure may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the disclosure encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions of the disclosure is packaged in a hermetically sealed container such as an ampoule or sachette indicating the quantity of the agent. In one embodiment, one or more of the prophylactic or therapeutic agents, or pharmaceutical compositions of the disclosure is supplied as a dry sterilized lyophilized powder or water free concentrate in a hermetically sealed container and can be reconstituted (e.g., with water or saline) to the appropriate concentration for administration to a subject. In another embodiment, one or more of the prophylactic or therapeutic agents or pharmaceutical compositions of the disclosure is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the disclosure should be stored at between 2.degree. C. and 8.degree. C. in its original container and the prophylactic or therapeutic agents, or pharmaceutical compositions of the disclosure should be administered within 1 week, within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the disclosure is supplied in liquid form in a hermetically sealed container indicating the quantity and concentration of the agent. In another embodiment, the liquid form of the administered composition is supplied in a hermetically sealed container at least 0.25 mg/ml, at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2.degree. C. and 8.degree. C. in its original container.

The antibodies and antibody-portions of the disclosure can be incorporated into a pharmaceutical composition suitable for parenteral administration. In another embodiment, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the disclosure prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

The compositions of this disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. In another embodiment, typical compositions are in the form of injectable or infusible solutions, such as compositions similar to those used for passive immunization of humans with other antibodies. In another embodiment, the mode of administration is parenteral (e.g., intravenous, subcutaneous, intraperitoneal, intramuscular). In another embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In another embodiment, in the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present disclosure can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody or antibody portion of the disclosure may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the disclosure by other than parenteral administration, it may be necessary to coat the compound with, or co-administer the compound with, a material to prevent its inactivation.

Supplementary active compounds can also be incorporated into the compositions. In certain embodiments, an antibody or antibody portion of the disclosure is coformulated with and/or coadministered with one or more additional therapeutic agents that are useful for treating disorders in which 4-1BB activity is too low. For example, an anti-4-1BB antibody or antibody portion of the disclosure may be coformulated and/or coadministered with one or more additional antibodies that bind other targets (e.g., antibodies that bind other cytokines or that bind cell surface molecules). Furthermore, one or more antibodies of the disclosure may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to 4-1BB or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the disclosure or another prophylactic or therapeutic agent of the disclosure are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the disclosure, the nucleic acids produce their encoded antibody or prophylactic or therapeutic agent of the disclosure that mediates a prophylactic or therapeutic effect.

Any of the methods for gene therapy available in the art can be used according to the present disclosure. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy is disclosed in US20050042664 A1 which is incorporated herein by reference.

Antibodies of the disclosure, or antigen binding portions thereof can be used alone or in combination to treat such diseases. It should be understood that the antibodies of the disclosure or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present disclosure. The additional agent also can be an agent that imparts a beneficial attribute to the therapeutic composition e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the present disclosure and at least one additional agent selected from the lists below. The combination can also include more than one additional agent, e.g., two or three additional agents if the combination is such that the formed composition can perform its intended function.

The combination therapy can include one or more 4-1BB agonists or antagonists, e.g., anti-4-1BB antibodies or fragments thereof, coformulated with, and/or coadministered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, as described in more herein.

The pharmaceutical compositions of the disclosure may include a "therapeutically effective amount" or a "prophylactically effective amount" of an antibody or antibody portion of the disclosure. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the disclosure is 0.1-20 mg/kg, 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the present disclosure in detail, the same will be more clearly understood by reference to the following examples, which are included for purposes of illustration only and are not intended to be limiting of the disclosure.

EXAMPLES

Example 1 Generation of Anti-Human 4-1BB Monoclonal Antibodies

Human antigens were selected and generated for immunization of animals. A DNA sequence encoding the N-terminal fragment (Met 1-Gln 186) of the extracellular domain of human 4-1BB (a.k.a. CD137) (NP_001552.2) was fused with the C terminal polyhistidine-tagged Fc region of human IgG1 at the C-terminus. The construct was introduced into host cells (e.g., Mouse myeloma cell line, NS0 derived) and expressed as a recombinant protein in the host cells. The recombinant protein was purified to a purity greater than 95% as determined by SDS-PAGE.

The domain structure of the protein is: N-terminus {{Human 4-1BB (Leu24-Gln186)-DIEGRMD-Human IgG1 (Pro100-Lys330)-6-His tag}} C-terminus. The Predicted Molecular weight (MW) is 44.8 kDa (monomer), and the MW as measure on SDS-PAGE is 50-65 KD.

The recombinant protein was shown to possess some of the functional property of 4-1BB as measured by its binding ability in a functional ELISA. When recombinant human 4-1BB Fc chimera is immobilized at 10 ng/mL (100 µL/well), the concentration of recombinant human 4-1BB Ligand (Catalog #2295-4L) that produces 50% optimal binding response is found to be approximately 0.5-2.5 ng/mL. Immobilized recombinant mouse 4-1BB Ligand at 20 µg/ml (100 µl/well) can bind human 4-1BB with a linear range of 15.6-500 ng/ml.

Mouse hybridoma screening was performed by using ELISA and confirmed by Western Blot. Binding affinity of selected clones was confirmed by cell surface binding assays. HEK293T cells were transfected with control or human/monkey 4-1BB plasmid overnight before being stained for 4-1BB mAb supernatants. Majority of selected clones showed cross-reactivity with human and monkey 4-1BB protein.

Example 2 Characterization of Anti-Human 4-1BB Monoclonal Antibodies

Plate-coated CD3 mAb costimulation. A 96-well culture plate was coated with different concentration of CD3 mAb (OKT3) in 1×PBS overnight. After washing with 1×PBS three times, the plate was further coated with 10 ug/ml h4-1BB mAb or control mouse IgG1 at the beginning of culture. Human T cells were isolated from human peripheral mononuclear cells (PBMCs), and were labeled with CFSE (Carboxyfluorescein succinimidyl ester) before being added into the antibody-coated plate. After 4-6 days culture, T cell division (or proliferation) was examined by CFSE dilution via flow cytometry.

Several clones were selected by their capability to stimulate T Cells proliferation. These clones may act as a co-stimulatory agonist of 4-1BB. One of these clones was ZW103. ZW103 was capable of expanding CD4+ T cell or CD8+ T cell in conjunction with one or more co-stimulator(s) (FIG. 1). Other clones include ZW104, ZW106, and ZW107, among others.

Figure 2:
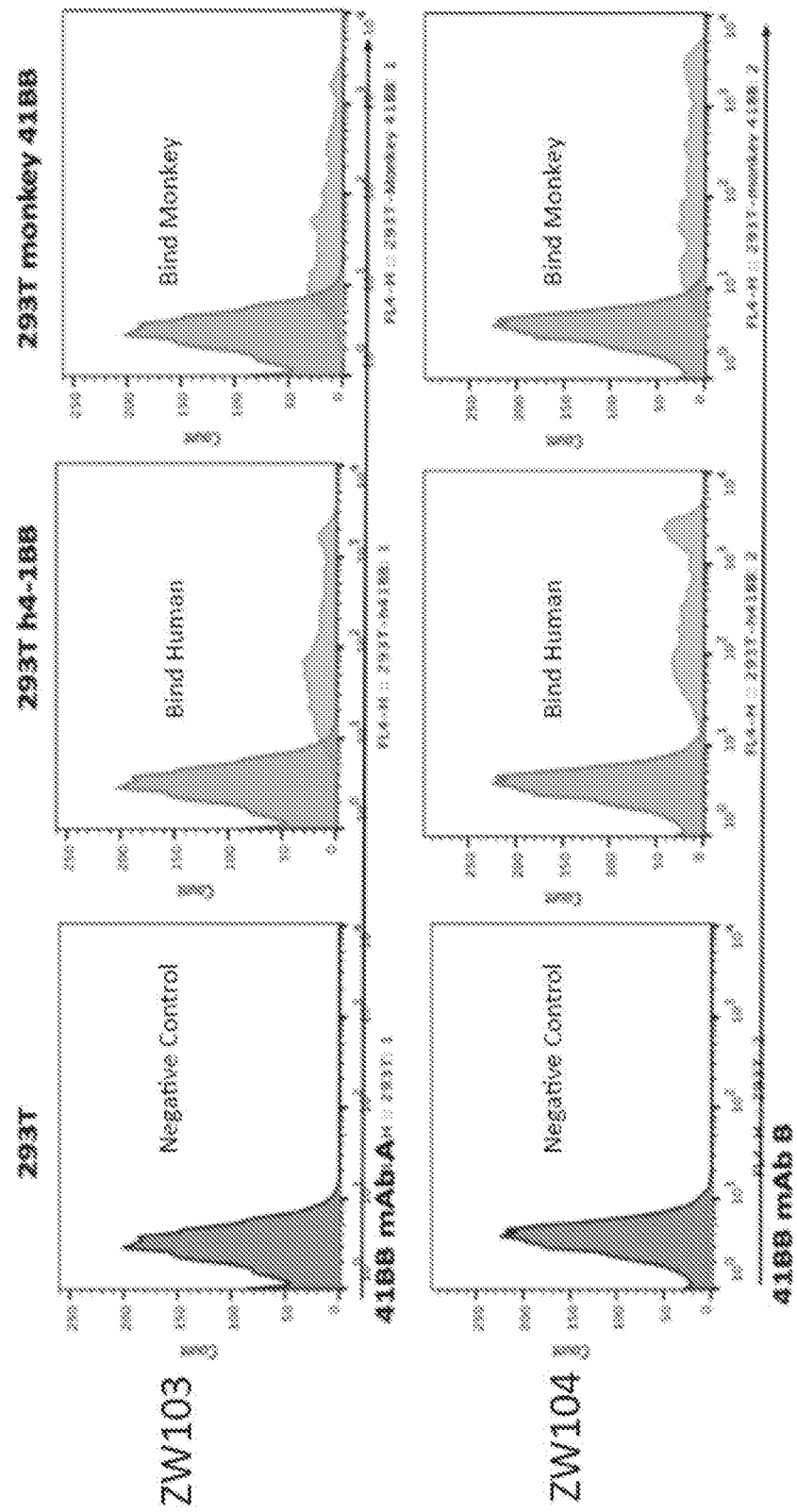
FIG. 2 shows that ZW103 and ZW104 (other clones show similar effect (data not shown)) are capable of binding human and monkey 4-1BB.

To confirm that the selected clones are capable of binding human and monkey 4-1BB, 293T cells expressing human or monkey 4-1BB were used to test binding of ZW103 and ZW104 to human and monkey 4-1BB. Both ZW103 and ZW104 were capable of binding human and monkey 4-1BB (FIG. 2). ZW106 and ZW107 were also capable of binding human and monkey 4-1BB. Table 8 shows the binding affinity of ZW106 with recombinant human 4-1BB ECD protein.

TABLE 8

| Binding affinity of the antibody clones | | | | | | | |
|---|---|---|---|---|---|---|---|
| Sample ID | Conc. (nM) | Response | KD (M) | KD Error | Kon (1/Ms) | Kon Error | Kdis (1/s) |
| ZW103 | 133.3 | 0.3184 | 2.645E−10 | — | 8.05E+05 | — | 2.13E−04 |
| ZW104 | 133.3 | 0.5541 | 4.745E−11 | — | 2.01E+05 | — | 9.52E−06 |

TABLE 8-continued

Binding affinity of the antibody clones

| Sample ID | Conc. (nM) | Response | KD (M) | KD Error | Kon (1/Ms) | Kon Error | Kdis (1/s) |
|---|---|---|---|---|---|---|---|
| ZW106 | 109.6 | 1.5702 | 1.20E−09 | 1.57E−10 | 8.78E+04 | 7.53E+02 | 1.05E−04 |
| ZW107 | 133.3 | 0.4192 | <1.0E−12 | — | 5.95E+05 | — | <1.0E−07 |

Figure 3:
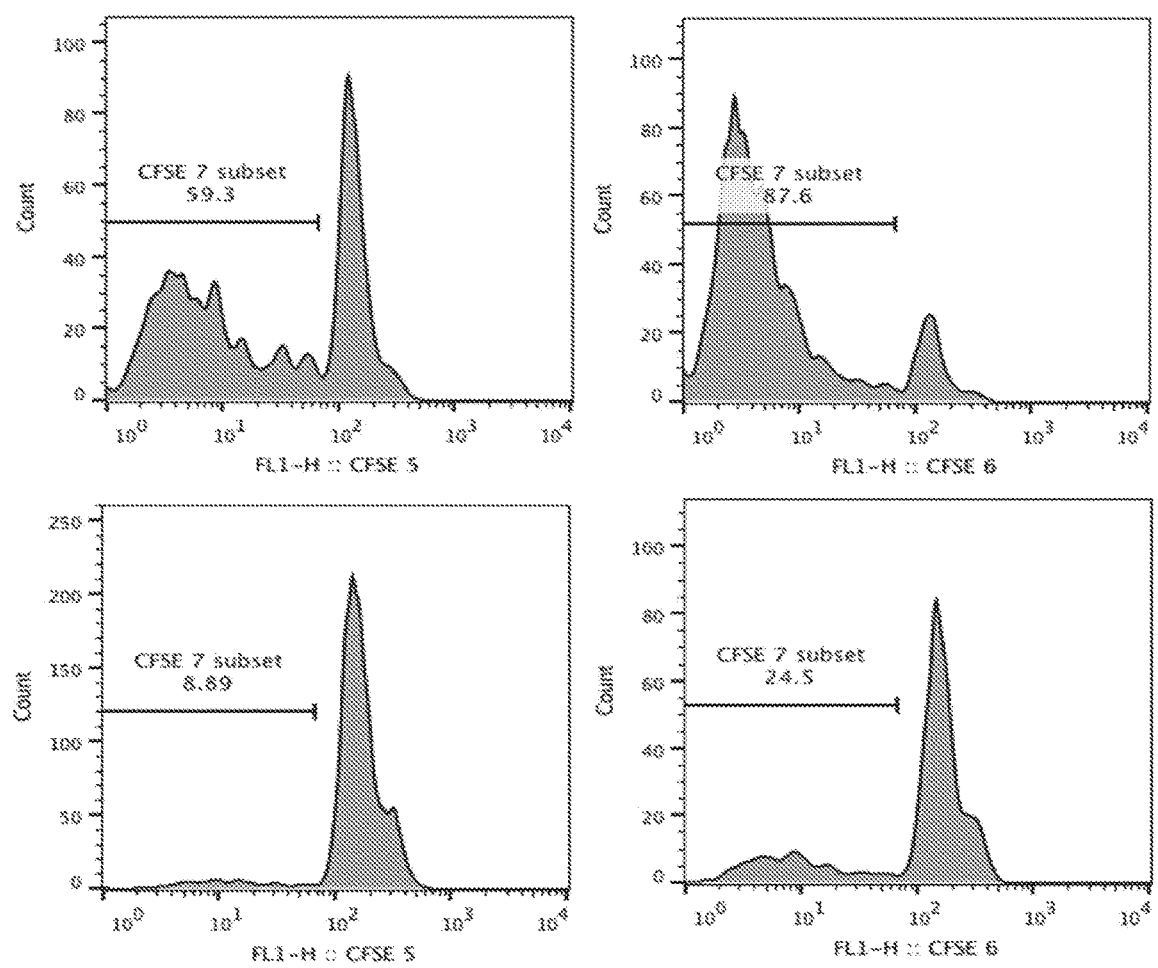
FIG. 3 shows that ZW103 and ZW104 (other clones show similar effect (data not shown)) are capable of stimulating T cell proliferation.

To confirm that the selected clones are capable of stimulate T cell proliferation in the presence of co-stimulator CD3 mAB, co-stimulation assays were performed in coated plates. Both ZW103 and ZW104 were capable of stimulating T cell proliferation (FIG. 3). Purified human T cells were CFSE-labeled, and stimulated with OKT3 together with coated 4-1BB mAb or control protein. Cells were harvested and stained for CD4 and CD8 after 5 days culture for flow cytometry analysis. The CFSE diluted cells indicated were counted as divided T cells (FIG. 3).

Figure 4:
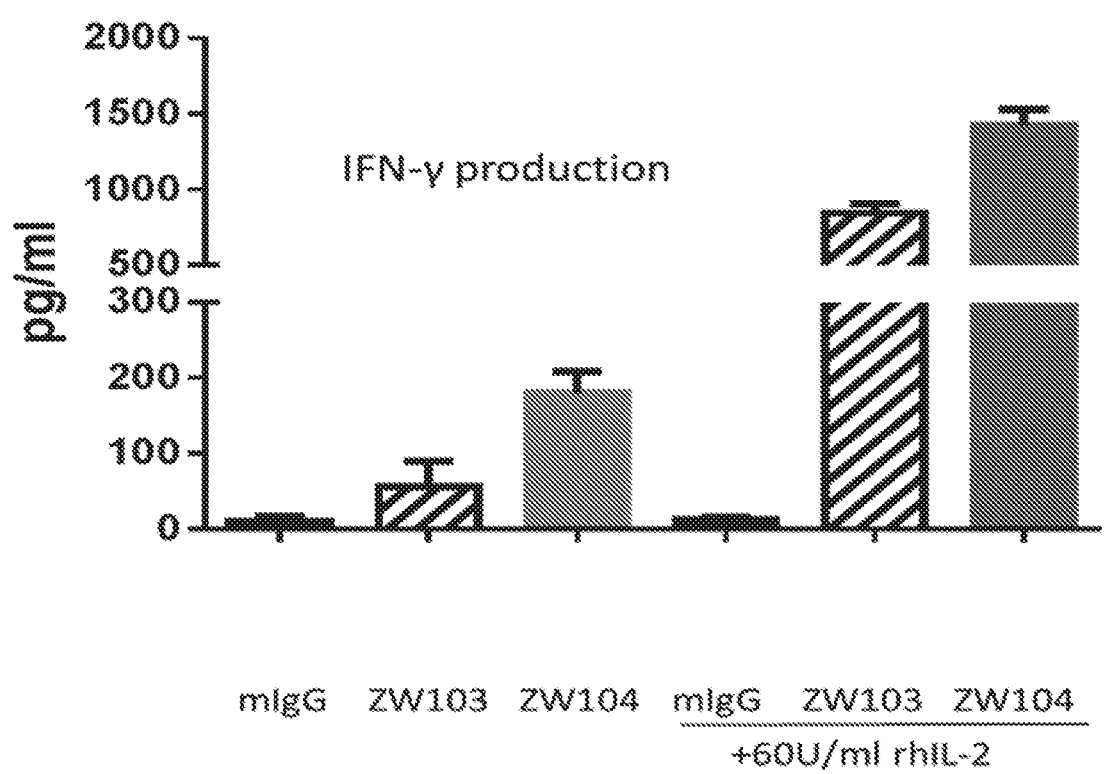
FIG. 4 shows that ZW103 and ZW104 (other clones show similar effect (data not shown)) are capable of activating human CD8+ and CD4+ T cells and stimulating production of IFN-gamma by human T cells.

FIG. 4 are graphs showing purified human T cells were stimulated with OKT3 together with coated 4-1BB mAbs or control protein. Recombinant human interleukin-2 (60 IU/ml) was added in some culture to boost T cell response. Supernatants were collected on day 5 to measure cytokine IFN-gamma (FIG. 4). These results confirmed that the selected clones are capable of activating human CD8+ and CD4+ T cells and stimulating production of IFN-gamma by human T cells.

Figure 5A:
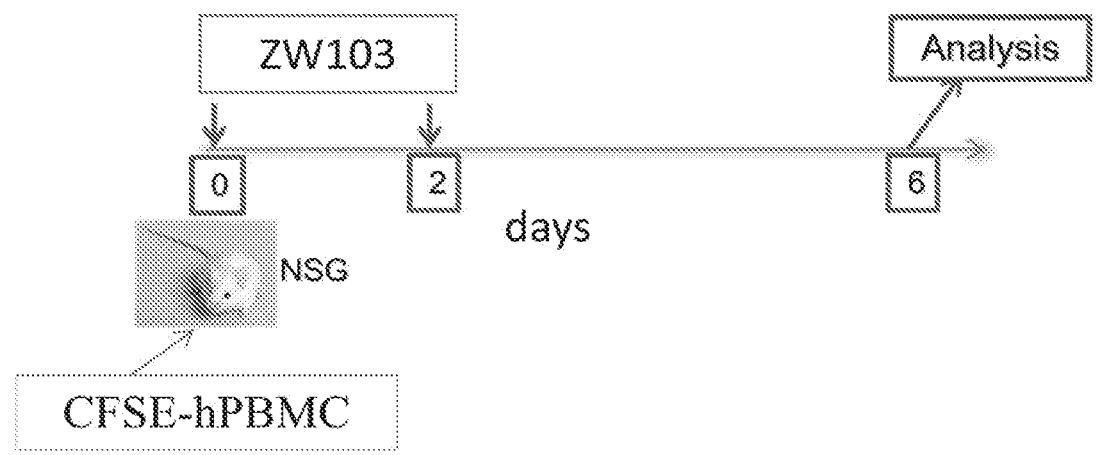
FIG. 5A shows the procedure of graft versus host (GVH) disease model.
Figure 5B:
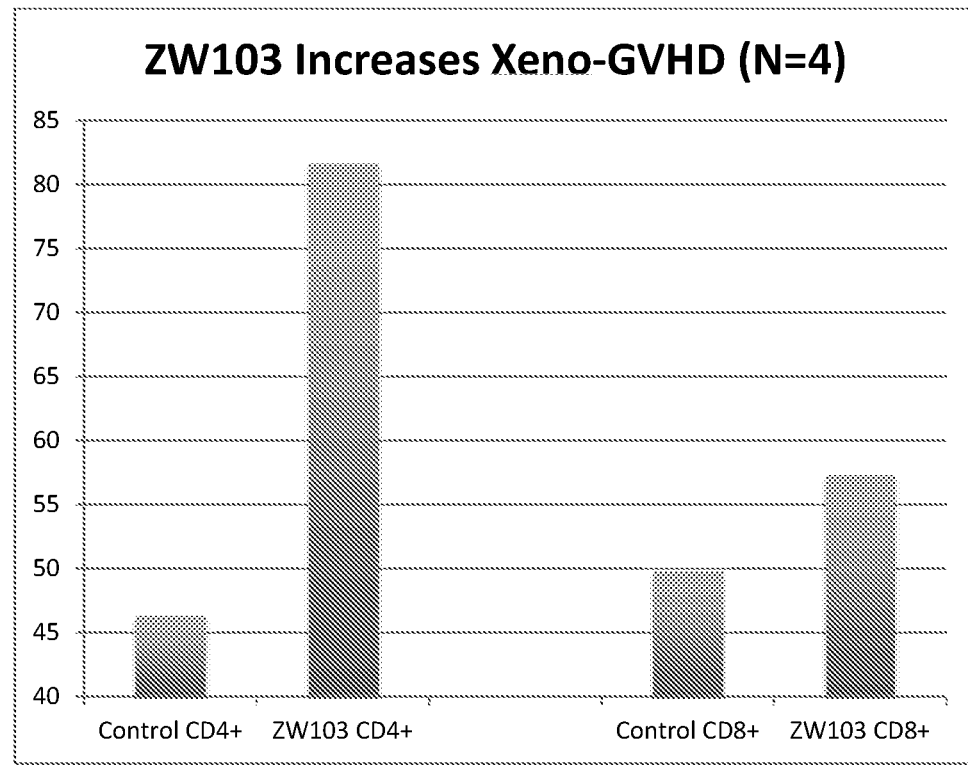
FIG. 5B shows 4-1BB mAb treatment promotes T cell proliferation in an xeno-GVHD mouse model.

FIG. 5A shows the procedure of graft versus host (GVH) disease model. On day 0, 10 million CFSE-labeled human peripheral blood mononuclear cells (PBMCs) were injected into NOD scid gamma (NSG) mouse. Mice were treated with 4-1BB mAb or control protein on day 0 and 2. Splenocytes were harvested on day 6 for flow cytometry analysis. As shown in FIG. 5B, 4-1BB mAb treatment promoted T cell proliferation in an xeno-GVHD mouse model. Splenocytes were harvested on day 6 and stained for hCD45, hCD3 and hCD8. Data shown are the average percentages of divided human T cells (N=4), determined by CFSE dilution. ZW103 enhanced immunity as evidenced by T cell proliferation in GVHD model (FIG. 5B).

Figure 6A:
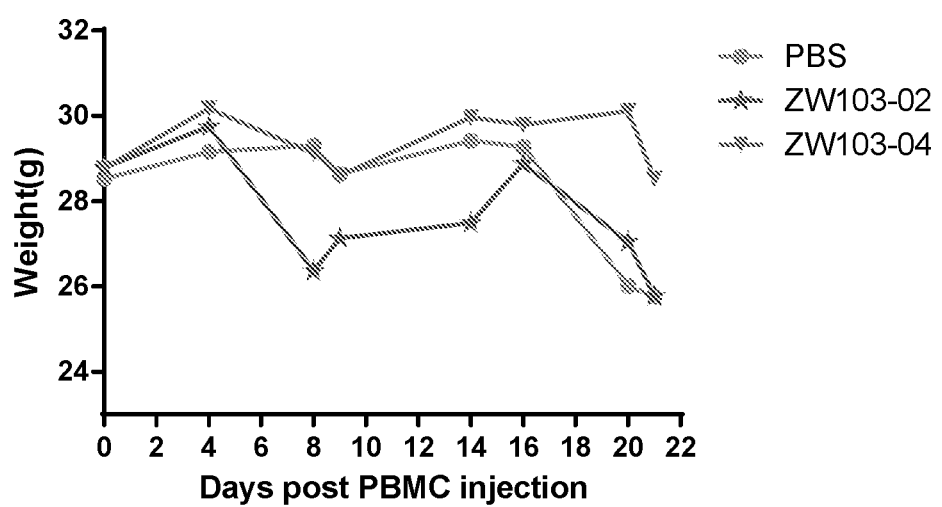
FIG. 6A shows the disclosed humanized 4-1BB Abs promoted the GVHD of NSG mice engrafted with human PBMC (FIG. 6A).

To test the effects of the disclosed 4-1BB Abs on GVHD of NSG mice engrafted with human PBMC, NSG injected with 15 million human PBMCs were treated with 300 µg of the disclosed humanized 4-1BB Abs or PBS controls on day 5, 8, 12, 15. Body weight was monitored upon hPBMC transfer. The result shows that the disclosed humanized 4-1BB Abs promoted the GVHD of NSG mice engrafted with human PBMC (FIG. 6A).

Figure 6B:
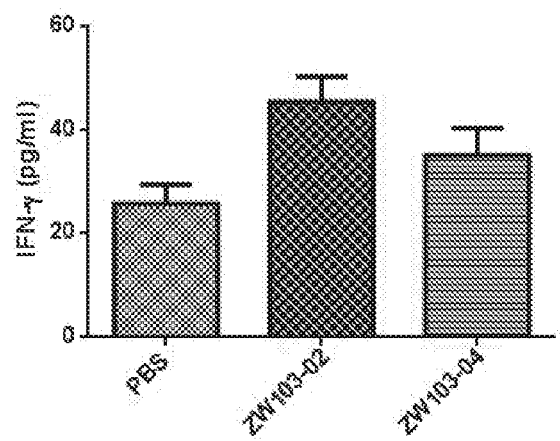
FIG. 6B shows that the disclosed humanized 4-1BB Abs increased serum IFN-γ in xeno-GVHD model.
Figure 6B:
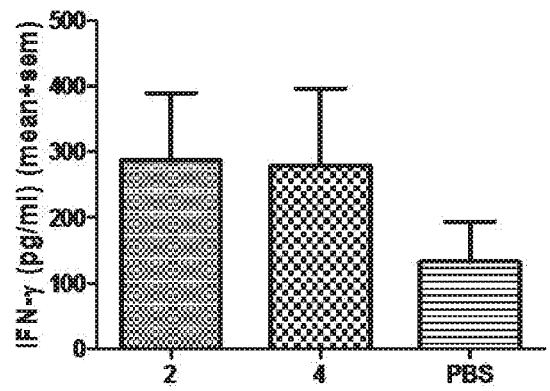

FIG. 6B shows that the disclosed humanized 4-1BB Abs increased serum IFN-γ in xeno-GVHD model. The top panel shows IFN-γ concentration in the serum as measured on day 8, and the lower panel shows IFN-γ concentration in the serum as measured on day 21 (the two bars on the left are ZW103-2 and ZW103-4, respectively, while the bar on the right is PBS).

Figure 6C:
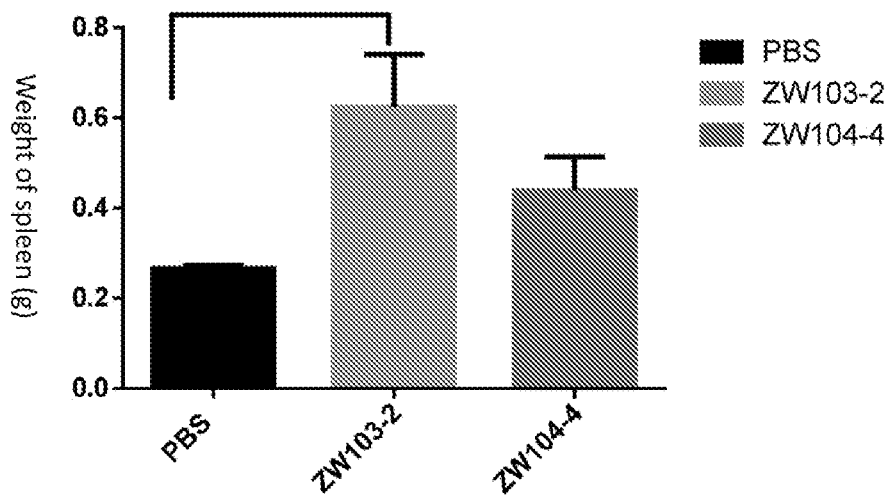
FIG. 6C shows that the disclosed humanized 4-1BB Abs increased spleen sizes in xeno-GVHD model.

FIG. 6C shows that the disclosed humanized 4-1BB Abs increased spleen sizes in xeno-GVHD model. As FIG. 4A, spleens were harvested and weighted on day 21.

Figure 6D:
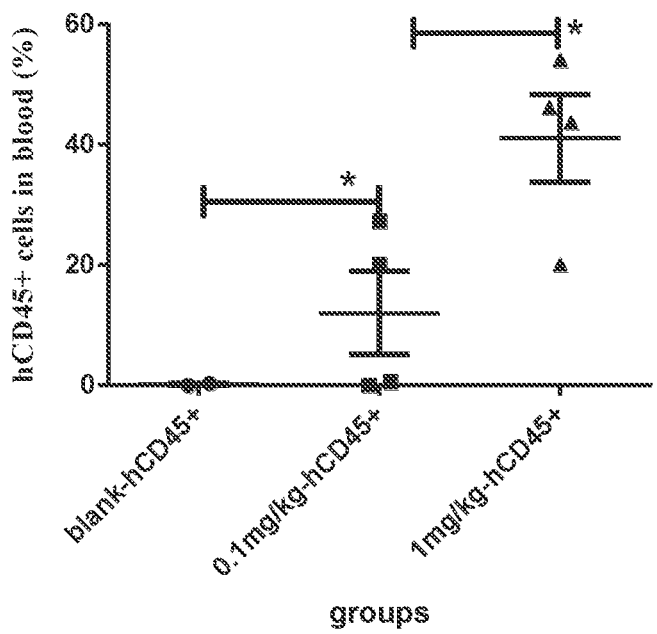
FIG. 6D shows that the disclosed humanized 4-1BB Abs increased human T cells in peripheral blood, and that the effect was dose-dependent.

FIG. 6D shows that the disclosed humanized 4-1BB Abs increased human T cells in peripheral blood, and that the effect was dose-dependent. As in FIG. 6A, engraftment of human PBMC was analyzed by FACS for human CD45 staining on day 28 following hPBMC transfer.

Figure 6E:
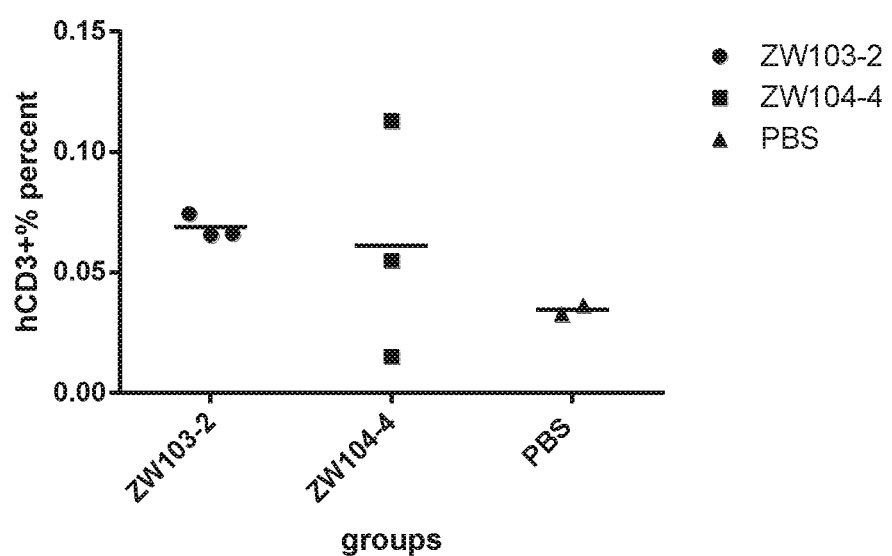
FIG. 6E shows that the disclosed humanized 4-1BB Abs increased human T cell infiltration in the liver.

FIG. 6E shows that the disclosed humanized 4-1BB Abs increased human T cell infiltration in the liver. As in FIG. 6A, 28 days after hPBMC transfer, liver tissue sections were stained with anti-human CD3 antibody.

Table 9 shows that the disclosed humanized 4-1BB Abs enhanced tissue injury caused by GVHD. As in FIG. 6A, on day 28, mice were sacrificed and tissues were immersed in 4% paraformaldehyde for hematoxylin and eosin (H&E) staining. Tissue injury was scored by two independent pathologists.

TABLE 9

The disclosed humanized 4-1BB Abs enhanced tissue injury caused by GVHD

| Groups | | Liver | Lung | Intestine |
|---|---|---|---|---|
| ZW103 | 2 | +++ | ++ | + |
|  | 3 | +++ | + | − |
|  | 4 | ++ | + | − |
| ZW104 | 5 | +++ | + | − |
|  | 6 | +++ | + | − |
|  | 8 | + | + | − |
| Blank Control | 9 | + | + | − |
|  | 11 | + | + | − |

Figure 7:
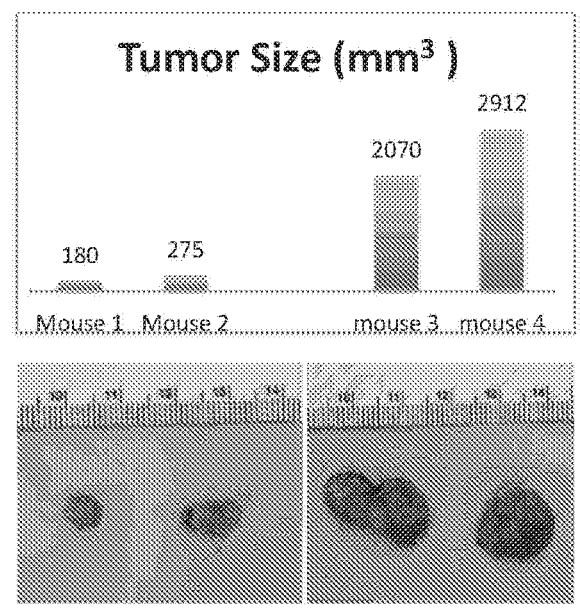
FIG. 7 shows the anti-tumor effect of human 4-1BB mAb in vivo.

FIG. 7 shows the antitumor effect of human 4-1BB mAb in vivo. Tumor model was created with subcutaneous injection of MC38 cancer cell ($0.5 \times 10^6$) to 4-1BB knock-in mice with a chimeric human 4-1BB extracellular gene. Mice were intravenously treated with 4-1BB mAb or control protein on day 5, 8, 12. Tumors were isolated and measured at day 18. The tumor sizes were significantly smaller in the group (Mouse 1 and Mouse 2) treated with ZW106, as compared to the control group (Mouse 3 and Mouse 4).

Example 3 Mapping of Epitope

To identify the epitopes of 4-1BB (CD137) ligand recognized by the purified antibody ZW 106 the precipitation of the trypsin and chymotrypsin digests of 4-1BB recombinant protein by the antibodies was performed. The precipitations were further detected by nano liquid chromatography tandem mass spectrometry (LC/MS/MS) analysis using Thermo Q-Exactive Orbitrap mass spectrometer. The results indicated that the peptide region of $T_{90}$KKGCKDCC FGTFNDQKRGICRPWTNCSLDGKSVL$_{124}$ (SEQ ID NO. 41) from the 4-1BB recombinant protein is the major epitope recognized by the antibody ZW106.

I claim:

1. A binding protein capable of specifically binding human CD137 (4-1BB), said binding protein comprising an antigen binding domain, said antigen binding domain comprising six CDRs: CDR-H1, CDR-H2, CDR-H3, CDR-L1, CDR-L2, and CDR-L3, wherein the six CDRs are selected from the group of variable domain CDR sets consisting of:

| VH ZW106 CDR Set | |
|---|---|
| CDR-H1: | SEQ ID NO: 21 |
| CDR-H2: | SEQ ID NO: 22 |
| CDR-H3: | SEQ ID NO: 23 |
| VL ZW106 CDR Set | |
| CDR-L1: | SEQ ID NO: 24 |
| CDR-L2: | SEQ ID NO: 25 |
| CDR-L3: | SEQ ID NO: 26. |

2. The binding protein according to claim 1, further comprising a human acceptor framework.

3. The binding protein according to claim 1, wherein said binding protein comprises at least one heavy chain variable domain and at least one light chain variable domain, said heavy chain variable domain having amino acid sequence selected from the group consisting of SEQ ID NOs: 5 and 42 and said light chain variable domain having amino acid sequence selected from the group consisting of SEQ ID NOs: 6 and 43.

4. The binding protein according to claim 3, wherein said binding protein comprises two variable domains, wherein said two variable domains have amino acid sequences selected from the group consisting of:

SEQ ID NOs:5 and 6; and
SEQ ID NOs:42 and 43.

5. The binding protein according to claim 1, further comprising a heavy chain immunoglobulin constant domain selected from the group consisting of: a human IgM constant domain; a human IgG1 constant domain; a human IgG2 constant domain; a human IgG3 constant domain; a human IgG4 constant domain; a human IgE constant domain and a human IgA constant domain.

6. The binding protein according to claim 5, wherein said heavy chain immunoglobulin constant domain is a human IgG1 constant domain.

7. The binding protein according to claim 1, further comprising a light chain immunoglobulin constant domain, wherein said light chain immunoglobulin constant domain is selected from the group consisting of a human Ig kappa constant domain and a human Ig lambda constant domain.

8. The binding protein according to claim 1 wherein said binding protein is selected from the group consisting of: an immunoglobulin molecule, an scFv, a monoclonal antibody, a human antibody, a chimeric antibody, a humanized antibody, a single domain antibody, a Fab fragment, a Fab' fragment, an F(ab')₂, an Fv, a disulfide linked Fv, a single domain antibody, a diabody, a multispecific antibody, a bispecific antibody, and a dual specific antibody.

9. The binding protein according to claim 1, wherein said binding protein is a human antibody.

10. The binding protein according to claim 1, wherein the binding protein is capable of modulating a biological function or levels of 4-1BB.

11. The binding protein according to claim 1, wherein said 4-1BB is human 4-1BB.

12. The binding protein according to claim 5, wherein the heavy chain immunoglobulin constant domain comprises a polypeptide having a sequence of SEQ ID No. 44.

13. The binding protein according to claim 7, wherein the light chain immunoglobulin constant domain comprises a polypeptide having a sequence of SEQ ID No. 45.

14. A binding protein capable of specifically binding human CD137 (4-1BB), said binding protein comprising a polypeptide having a sequence of SEQ ID No. 42, a polypeptide having a sequence of SEQ ID No. 43, a polypeptide having a sequence of SEQ ID No. 44, and a polypeptide having a sequence of SEQ ID No. 45.

15. An antibody construct comprising a binding protein described in claim 1 and further comprising a linker polypeptide or an immunoglobulin constant domain.

16. The antibody construct according to claim 15, selected from the group consisting of:
an immunoglobulin molecule,
a monoclonal antibody,
a chimeric antibody,
a CDR-grafted antibody,
a humanized antibody,
a Fab,
a Fab',
a F(ab')$_2$,
a Fv,
a disulfide linked Fv,
a scFv,
a diabody,
a multispecific antibody,
a dual specific antibody, and
a bispecific antibody.

17. The antibody construct according to claim 16, wherein said antibody construct comprises a heavy chain immunoglobulin constant domain selected from the group consisting of:
a human IgM constant domain,
a human IgG1 constant domain,
a human IgG2 constant domain,
a human IgG3 constant domain,
a human IgG4 constant domain,
a human IgE constant domain,
a human IgA constant domain,
and
an IgG constant domain variant with one or more mutations altering binding strength to Fc neonatal receptor, Fc gamma receptors, or C1q.

18. A pharmaceutical composition comprising the binding protein of claim 1, and a pharmaceutically acceptable carrier.

19. A method for altering human CD137 14-1 BB) activity, comprising contacting human CD137 (4-1 BB) with the binding protein of claim 1 at a dosage effective in altering human CD137 (4-1BB) activity.

* * * * *

SEQUENCE LISTING

<160> NUMBER OF SEQ ID NOS: 45

<210> SEQ ID NO 1
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Val Lys Ser Leu Glu Trp Ile
            35                  40                  45

Gly Gly Ile Ser Thr Tyr Asn Gly Asp Ala Ser Tyr Asn Gln Lys Phe
        50                  55                  60

Lys Gly Lys Ala Thr Met Thr Val Asp Lys Ser Ser Arg Thr Ala Tyr
65                  70                  75                  80

Met Glu Leu Val Arg Leu Thr Ser Glu Asp Ser Ala Ile Tyr Tyr Cys
                85                  90                  95

Ala Pro Ser Asn Tyr Gly Tyr Ala Met Asp Tyr Trp Gly Gln Gly Thr
            100                 105                 110

Ser Val Thr Val Ser Ser
        115

<210> SEQ ID NO 2
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 2

Asp Ile Val Met Ser Gln Ser Pro Ser Ser Leu Ala Val Ser Val Gly
1               5                   10                  15

Glu Lys Val Ser Val Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Leu Ser Tyr Pro Trp Thr Phe Gly Gly Gly Thr Lys Leu Glu Ile
            100                 105                 110

Asn

<210> SEQ ID NO 3
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 3

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Ile Phe Thr Thr Tyr
            20                  25                  30

Ala Met His Trp Val Lys Gln Arg Pro Gly Gln Gly Leu Glu Trp Ile
        35                  40                  45

Gly Tyr Ile Asn Pro Thr Thr Val Tyr Thr Ile Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Gly His Trp Tyr Phe Asp Val Trp Gly Ala Gly Thr
                100                 105                 110

Thr Val Thr Val Ser Ser
                115
```

<210> SEQ ID NO 4
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 4

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ser Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
                100                 105                 110
```

<210> SEQ ID NO 5
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 5

```
Gln Val Gln Leu Gln Gln Pro Glu Ser Glu Leu Val Arg Pro Gly Gly
1               5                   10                  15

Ser Val Lys Leu Ser Cys Lys Ala Ser Gly Tyr Thr Phe Thr Ser Tyr
            20                  25                  30

Trp Met Asp Trp Val Lys Gln Arg His Gly Gln Gly Leu Glu Trp Ile
        35                  40                  45

Gly Asn Ile Tyr Pro Asp Ser Gly Gly Thr Asn Tyr Ala Glu Lys Phe
    50                  55                  60

Lys Ser Lys Ala Thr Leu Thr Val Asp Thr Ser Ser Ser Thr Ala Tyr
65                  70                  75                  80
```

Met His Leu Ser Ser Leu Thr Ser Glu Asp Ser Ala Val Tyr Tyr Cys
            85                  90                  95

Thr Arg Glu Glu Ala Leu Gly Gly Tyr Tyr Glu Leu Thr Tyr Trp Gly
        100                 105                 110

Gln Gly Thr Leu Val Thr Val Ser Ala
        115                 120

<210> SEQ ID NO 6
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 6

Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Glu
            100                 105                 110

<210> SEQ ID NO 7
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 7

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Ala Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Asn Gly Asn Asn Tyr Tyr Ser Glu Lys Phe
    50                  55                  60

Lys Asp Lys Ala Thr Leu Thr Ala Asp Lys Ser Ser Ser Thr Val Tyr
65                  70                  75                  80

Ile Arg Leu Ser Ser Leu Thr Ser Glu Asp Ser Ala Val Tyr Phe Cys
                85                  90                  95

Ala Arg His Gly Ser Phe Arg Ser Ala Met Asp Tyr Trp Gly Gln Gly
            100                 105                 110

Thr Ser Val Thr Val Ser Ser
        115

<210> SEQ ID NO 8
<211> LENGTH: 107
<212> TYPE: PRT

<213> ORGANISM: Artificial Sequence
<220> FEATURE:
<223> OTHER INFORMATION: Synthetic polypeptide

<400> SEQUENCE: 8

Asp Ile Gln Met Thr Gln Ser Pro Ala Ser Pro Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

Asp Tyr Ala Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 10

Gly Ile Ser Thr Tyr Asn Gly Asp Ala Ser Tyr Asn Gln Lys Phe Lys
1               5                   10                  15

Gly

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Ser Asn Tyr Gly Tyr Ala Met Asp Tyr
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 12

Lys Ser Ser Gln Ser Leu Leu Tyr Ser Ser Asn Gln Lys Asn Tyr Leu

```
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 13

Trp Ala Ser Thr Arg Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 14

Gln Gln Tyr Leu Ser Tyr Pro Trp Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 15

Thr Tyr Ala Met His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 16

Tyr Ile Asn Pro Thr Thr Val Tyr Thr Ile Tyr Asn Gln Lys Phe Lys
1               5                   10                  15

Asp

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Leu Gly Gly His Trp Tyr Phe Asp Val
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic polypeptide
```

```
<400> SEQUENCE: 18

Arg Ala Ser Glu Ser Val Asp Asn Tyr Gly Ile Ser Phe Met Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

Ser Ala Ser Asn Gln Gly Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 20

Gln Gln Ser Lys Glu Val Pro Trp Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 21

Ser Tyr Trp Met Asp
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 22

Asn Ile Tyr Pro Asp Ser Gly Gly Thr Asn Tyr Ala Glu Lys Phe Lys
1               5                   10                  15
Ser

<210> SEQ ID NO 23
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 23

Glu Glu Ala Leu Gly Gly Tyr Tyr Glu Leu Thr Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic polypeptide
```

<400> SEQUENCE: 24

Arg Ala Ser Gln Ser Val Ser Thr Ser Ser Tyr Ser Tyr Met His
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 25

Tyr Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 26

Gln His Ser Trp Glu Ile Pro Tyr Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 27

Asn Tyr Trp Leu Gly
1               5

<210> SEQ ID NO 28
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 28

Asp Ile Tyr Pro Gly Asn Gly Asn Asn Tyr Tyr Ser Glu Lys Phe Lys
1               5                   10                  15

Asp

<210> SEQ ID NO 29
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 29

His Gly Ser Phe Arg Ser Ala Met Asp Tyr
1               5                   10

<210> SEQ ID NO 30
<211> LENGTH: 11
<212> TYPE: PRT
<213> ORGANISM: Artificial Sequence
<220> FEATURE:

```
<223> OTHER INFORMATION: Synthetic polypeptide

<400> SEQUENCE: 30

Arg Ala Ser Glu Asn Ile Tyr Ser Tyr Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 31

Asn Ala Lys Thr Leu Ala Asp
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 32

Gln His His Tyr Gly Thr Pro Pro Thr
1               5

<210> SEQ ID NO 33
<211> LENGTH: 137
<212> TYPE: PRT
<213> ORGANISM: Artificial Sequence
<220> FEATURE:
<223> OTHER INFORMATION: Synthetic polypeptide

<400> SEQUENCE: 33

Met Gly Trp Ser Cys Ile Ile Val Phe Leu Val Ala Thr Ala Thr Gly
1               5                   10                  15

Val His Ser Gln Val Gln Leu Gln Gln Ser Gly Ala Glu Leu Val Arg
                20                  25                  30

Pro Gly Val Ser Val Lys Ile Ser Cys Lys Gly Ser Gly Tyr Thr Phe
            35                  40                  45

Thr Asp Tyr Ala Met His Trp Val Lys Gln Ser His Val Lys Ser Leu
        50                  55                  60

Glu Trp Ile Gly Gly Ile Ser Thr Tyr Asn Gly Asp Ala Ser Tyr Asn
65                  70                  75                  80

Gln Lys Phe Lys Gly Lys Ala Thr Met Thr Val Asp Lys Ser Ser Arg
                85                  90                  95

Thr Ala Tyr Met Glu Leu Val Arg Leu Thr Ser Glu Asp Ser Ala Ile
            100                 105                 110

Tyr Tyr Cys Ala Pro Ser Asn Tyr Gly Tyr Ala Met Asp Tyr Trp Gly
        115                 120                 125

Gln Gly Thr Ser Val Thr Val Ser Ser
        130                 135

<210> SEQ ID NO 34
<211> LENGTH: 133
<212> TYPE: PRT
<213> ORGANISM: Artificial Sequence
<220> FEATURE:
<223> OTHER INFORMATION: Synthetic polypeptide

<400> SEQUENCE: 34
```

```
Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Ser Val Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Leu Ser Tyr Pro Trp Thr Phe Gly Gly Gly Thr
        115                 120                 125

Lys Leu Glu Ile Asn
    130

<210> SEQ ID NO 35
<211> LENGTH: 137
<212> TYPE: PRT
<213> ORGANISM: Artificial Sequence
<220> FEATURE:
<223> OTHER INFORMATION: Synthetic polypeptide

<400> SEQUENCE: 35

Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Ile Phe
        35                  40                  45

Thr Thr Tyr Ala Met His Trp Val Lys Gln Arg Pro Gly Gln Gly Leu
    50                  55                  60

Glu Trp Ile Gly Tyr Ile Asn Pro Thr Thr Val Tyr Thr Ile Tyr Asn
65                  70                  75                  80

Gln Lys Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Leu Gly Gly His Trp Tyr Phe Asp Val Trp Gly
        115                 120                 125

Ala Gly Thr Thr Val Thr Val Ser Ser
    130                 135

<210> SEQ ID NO 36
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 36

Met Glu Lys Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
```

```
            20                  25                  30

Val Ser Leu Gly Gln Arg Ala Thr Ile Ser Cys Arg Ala Ser Glu Ser
        35                  40                  45

Val Asp Asn Tyr Gly Ile Ser Phe Met Asn Trp Phe Gln Gln Lys Pro
    50                  55                  60

Gly Gln Pro Pro Lys Leu Leu Ile Tyr Ser Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Ser Lys Glu Val Pro Trp Thr Phe Gly Gly Gly Thr Lys Leu
        115                 120                 125

Glu Ile Lys
        130

<210> SEQ ID NO 37
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 37

Met Gly Trp Ser Cys Ile Ile Leu Phe Leu Val Ala Thr Ala Thr Gly
1               5                   10                  15

Val His Ser Gln Val Gln Leu Gln Gln Pro Glu Ser Glu Leu Val Arg
            20                  25                  30

Pro Gly Gly Ser Val Lys Leu Ser Cys Lys Ala Ser Gly Tyr Thr Phe
        35                  40                  45

Thr Ser Tyr Trp Met Asp Trp Val Lys Gln Arg His Gly Gln Gly Leu
    50                  55                  60

Glu Trp Ile Gly Asn Ile Tyr Pro Asp Ser Gly Gly Thr Asn Tyr Ala
65                  70                  75                  80

Glu Lys Phe Lys Ser Lys Ala Thr Leu Thr Val Asp Thr Ser Ser Ser
                85                  90                  95

Thr Ala Tyr Met His Leu Ser Ser Leu Thr Ser Glu Asp Ser Ala Val
            100                 105                 110

Tyr Tyr Cys Thr Arg Glu Glu Ala Leu Gly Gly Tyr Tyr Glu Leu Thr
        115                 120                 125

Tyr Trp Gly Gln Gly Thr Leu Val Thr Val Ser Ala
    130                 135                 140

<210> SEQ ID NO 38
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 38

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Pro
            20                  25                  30

Val Ser Leu Gly Gln Arg Ala Thr Ile Ser Cys Arg Ala Ser Gln Ser
        35                  40                  45
```

Val Ser Thr Ser Ser Tyr Ser Tyr Met His Trp Tyr Gln Gln Lys Pro
            50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                    85                  90                  95

Leu Asn Ile His Pro Val Glu Glu Asp Thr Ala Thr Tyr Tyr Cys
                100                 105                 110

Gln His Ser Trp Glu Ile Pro Tyr Thr Phe Gly Gly Gly Thr Lys Leu
            115                 120                 125

Glu Ile Glu
    130

<210> SEQ ID NO 39
<211> LENGTH: 138
<212> TYPE: PRT
<213> ORGANISM: Artificial Sequence
<220> FEATURE:
<223> OTHER INFORMATION: Synthetic polypeptide

<400> SEQUENCE: 39

Met Glu Trp Ser Gly Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Ile Ser Cys Lys Ala Ser Gly Tyr Ala Phe
        35                  40                  45

Thr Asn Tyr Trp Leu Gly Trp Val Lys Gln Arg Pro Gly His Gly Leu
    50                  55                  60

Glu Trp Ile Gly Asp Ile Tyr Pro Gly Asn Gly Asn Asn Tyr Tyr Ser
65                  70                  75                  80

Glu Lys Phe Lys Asp Lys Ala Thr Leu Thr Ala Asp Lys Ser Ser Ser
                85                  90                  95

Thr Val Tyr Ile Arg Leu Ser Ser Leu Thr Ser Glu Asp Ser Ala Val
            100                 105                 110

Tyr Phe Cys Ala Arg His Gly Ser Phe Arg Ser Ala Met Asp Tyr Trp
        115                 120                 125

Gly Gln Gly Thr Ser Val Thr Val Ser Ser
    130                 135

<210> SEQ ID NO 40
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 40

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Pro Ser
            20                  25                  30

Ala Ser Val Gly Glu Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Phe Ser Leu Lys Ile Asn
            85                  90                  95

Ser Leu Gln Pro Glu Asp Phe Gly Ser Tyr Tyr Cys Gln His His Tyr
                100                 105                 110

Gly Thr Pro Pro Thr Phe Gly Gly Thr Lys Leu Glu Ile Lys
            115                 120                 125

<210> SEQ ID NO 41
<211> LENGTH: 35
<212> TYPE: PRT
<213> ORGANISM: Homo sapiens

<400> SEQUENCE: 41

Thr Lys Lys Gly Cys Lys Asp Cys Cys Phe Gly Thr Phe Asn Asp Gln
1               5                   10                  15

Lys Arg Gly Ile Cys Arg Pro Trp Thr Asn Cys Ser Leu Asp Gly Lys
                20                  25                  30

Ser Val Leu
        35

<210> SEQ ID NO 42
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asp Trp Val Arg Gln Ala Pro Gly Gln Gly Leu Glu Trp Met
            35                  40                  45

Gly Asn Ile Tyr Pro Asp Ser Gly Gly Thr Asn Tyr Ala Glu Lys Phe
        50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Glu Ala Leu Gly Gly Tyr Tyr Glu Leu Thr Tyr Trp Gly
                100                 105                 110

Gln Gly Thr Leu Val Thr Val Ser Ser
            115                 120

<210> SEQ ID NO 43
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
                20                  25                  30

Ser Tyr Ser Tyr Met His Trp Tyr Gln Gln Lys Pro Gly Gln Pro Pro
            35                  40                  45

```
Lys Leu Leu Ile Lys Tyr Ala Ser Asn Leu Glu Ser Gly Val Pro Asp
         50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Trp
                 85                  90                  95

Glu Ile Pro Tyr Thr Phe Gly Gly Gly Thr Lys Val Glu Ile Lys
                100                 105                 110

<210> SEQ ID NO 44
<211> LENGTH: 327
<212> TYPE: PRT
<213> ORGANISM: Artificial Sequence
<220> FEATURE:
<223> OTHER INFORMATION: Synthetic polypeptide

<400> SEQUENCE: 44

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
             115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 45
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 45

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```